United States Patent
Arand et al.

(10) Patent No.: US 7,174,203 B2
(45) Date of Patent: Feb. 6, 2007

(54) METHOD AND SYSTEM RELATING TO MONITORING AND CHARACTERIZING HEART CONDITION

(75) Inventors: Patricia A. Arand, McMinnville, OR (US); Peter T. Bauer, West Linn, OR (US); Peter M. Galen, Portland, OR (US); Robert A. Warner, Tigard, OR (US)

(73) Assignee: Inovise Medical, Inc., Portland, OR (US)

( * ) Notice: Subject to any disclaimer, the term of this patent is extended or adjusted under 35 U.S.C. 154(b) by 176 days.

(21) Appl. No.: 10/993,521

(22) Filed: Nov. 18, 2004

(65) Prior Publication Data

US 2006/0106322 A1 May 18, 2006

(51) Int. Cl.
*A61B 5/04* (2006.01)
(52) U.S. Cl. .................... 600/513; 600/528
(58) Field of Classification Search .......... None
See application file for complete search history.

(56) References Cited

U.S. PATENT DOCUMENTS

| | | | |
|---|---|---|---|
| 4,840,183 A | 6/1989 | Takahashi et al. | |
| 5,086,776 A | 2/1992 | Fowler, Jr. et al. | 600/455 |
| 5,623,925 A | 4/1997 | Swenson et al. | 600/301 |
| 5,685,317 A | 11/1997 | Sjöström | 600/528 |
| 5,687,738 A | 11/1997 | Shapiro et al. | 600/528 |
| 5,957,866 A | 9/1999 | Shapiro et al. | 600/586 |
| 6,050,950 A | 4/2000 | Mohler | 600/485 |
| 6,527,729 B1 | 3/2003 | Turcott | |
| 2004/0220487 A1 | 11/2004 | Vyshedskiy et al. | |
| 2004/0260188 A1* | 12/2004 | Syed et al. | 600/509 |
| 2006/0047213 A1* | 3/2006 | Gavriely et al. | 600/513 |

\* cited by examiner

*Primary Examiner*—Carl Layno
(74) *Attorney, Agent, or Firm*—Jon M. Dickinson; Robert Varitz

(57) ABSTRACT

A method and a system for monitoring and characterizing a person's heart condition for various medically related purposes. The method includes the steps of (a) acquiring a selected person's acoustic heart signature, (b) acquiring, substantially simultaneously, that same person's electrical heart signature, (c) choosing elements of determined interest from these two acquired signatures and selectively processing and inter- and/or cross-relating such elements, and (d) employing the results of the relating step to create a heart-condition fingerprint useful in the characterization of that person's heart condition. From a systemic point of view, that system includes (a) acoustic and electrical data-gathering devices employable to collect acoustic and electrical data from a person, and (b) processing structure operatively connected to these devices, operable to process and inter- and/or cross-relate data gathered by the devices for the purpose of generating a reportable heart-condition fingerprint of a person from whom such data has been collected.

15 Claims, 30 Drawing Sheets

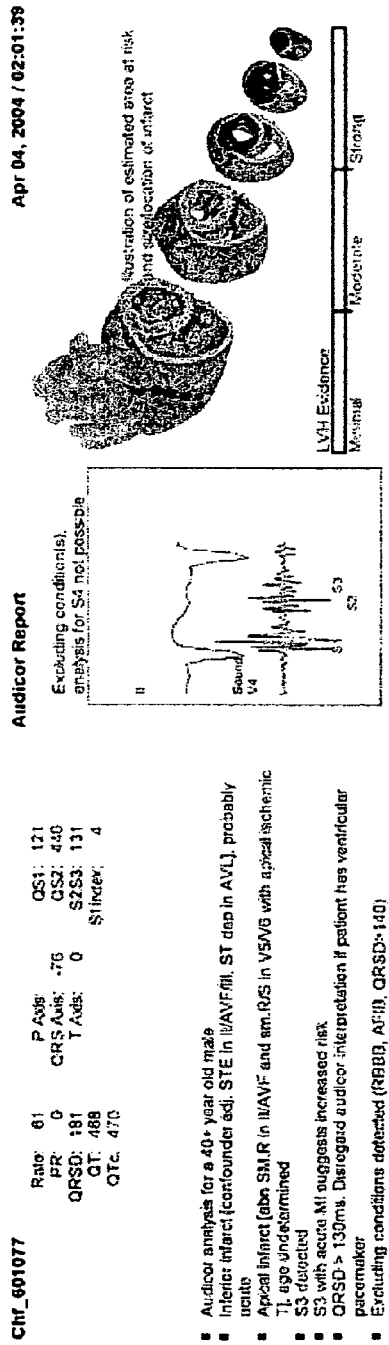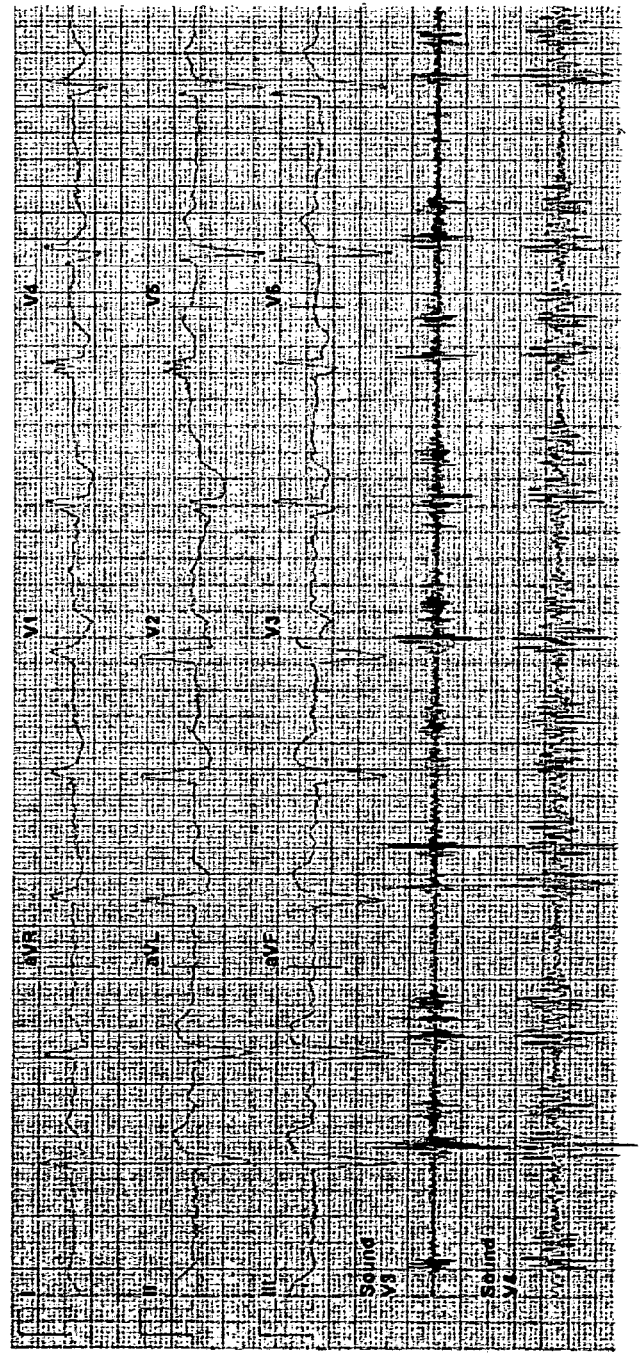
Fig. 8

Subject A

Heart rate

PR interval

QRS axis

QRS area

STJ20

S1 strength

S1 area in V3

S1 area in V4

S2 strength

S2 area in V3

S2 area in V3

S3 confidence

S4 confidence

S3 and S4 confidence (sum V3+V4)

S3 area in V3

S3 area in V4

S4 area in V3

S4 area in V4

Q-S1 in V3

Q-S1 in V4

Q-S2 in V3

Q-S2 in V4 r) Subject B

Heart rate

PR interval

QRS axis

QRS area

STJ20

S1 strength

S1 area in V3

S1 area in V4

S2 strength

S2 area in V3

S2 area in V3

S3 confidence

S3 area in V3

S3 area in V4

S4 area in V3

S4 area in V4

Q-S1 in V3

Q-S1 in V4

Q-S2 in V3

Q-S2 in V4

S1-S2 in V3

S1-S2 in V4

METHOD AND SYSTEM RELATING TO MONITORING AND CHARACTERIZING HEART CONDITION

BACKGROUND AND SUMMARY OF THE INVENTION

This invention relates to a method and a system for monitoring and characterizing a person's heart condition with respect to identifying different components of cardiac disease. Additionally, it relates to such a method and system wherein results from monitoring and characterizing activities can be employed for a number of purposes, including (a) diagnosis, (b) the creation of various kinds of currently useful and archival records, such as chart and electronic database records, and for (c) implementing various kinds of selectable control functions, such as controlling the operational behavior of a device like a pacemaker, and other.

In a sense, the present invention rests on an underlying concept which recognizes the special utility of gathering heart acoustical sounds (PCG modality) along with ECG data (ECG modality), and then measuring, evaluating and inter- and cross-relating and combining various components of these two kinds of data for the purpose of assessing various kinds of heart conditions. To simplify the concepts of inter- and cross-relating and combining will be understood to mean all such forms of sound/sound, ECG/ECG, sound/ECG, and ECG/sound data exploration.

As far as we are able to determine, where, in prior art practice, practitioners have gathered heart acoustical data, i.e., heart sounds along with ECG data (signatures), it has usually been the case that the heart-sound data is employed essentially only for various data timing purposes. In other words, we are unaware of any prior art proposal for gathering correlatable heart sounds and ECG data, and then processing these two kinds of data to develop a new kind of view into the status and behavior of a person's heart. A part of the underlying concept of this invention relates to locating and using features that are found in ECG information, along with features found in acoustic information, to improve understanding and diagnosis of the condition of a person's heart. It also recognizes the fact that these two kinds of data can be thought of as being "orthogonal" with respect to one another—"orthogonal" in the sense that they operate with relevance in different physical realms of heart activity. In this context, each of these two kinds of data can be characterized as possessing both "strengths and weaknesses" with respect to furnishing useful and important heart information. They are, in a sense, capable, when examined carefully, of providing very useful "complementary" information about heart condition. To deal with this situation, the invention, effectively, can be thought of as using the "strengths" contributed by one of these two kinds of data to "buttress the weaknesses" in the other kind of data, and vise versa. This, of course, is merely a stylized way of envisioning the "complementary" capabilities of these two data areas.

As will be well understood by those skilled in the art, heart sounds and heart ECG information each effectively takes a look at, or provides information about, different aspects of the heart. Respecting ECG information, the electrical activity of the heart is observed. This information, for example, gives data relevant to the health of cells, to characteristics of conduction pathways and speeds in the heart, and to various physical changes in the heart that are known to affect electrical heart activity. Other well known factors are also recognizably associated with ECG information.

Heart acoustic information looks primarily at physical mechanical and hydraulic properties of the heart (and of its chambers and valves), of blood, and of related vasculature.

Many cardiac conditions affect both the electrical and the acoustic signatures of the heart, and as will be seen, this invention makes unique use of possibilities for measuring, evaluating and relating and combining information drawn from these signatures to enhance heart-condition monitoring and assessment.

As brief illustrations of the promise and power of combining acoustical and electrical heart signatures, it is well known that the presence of the abnormal diastolic S4 or S3 heart sounds increases the odds of a correct determination that the associated person has ischemia—one important aspect or component of heart disease. When information relating to these abnormal heart sounds is combined with ECG information, a decidedly better diagnosis and interpretation relative to ischemia is possible.

Another example involves the fact that the S4 heart sound generally indicates a stiff left ventricle. As such, this increases the odds of either the existence of a prior myocardial infarct (PMI), or the presence of Left Ventricular Hypertrophy (LVH).

Further generally describing the present invention in the setting of its prior art landscape, heart sounds are acoustic phenomenon that are created due to vibrations within the heart and its structures. These vibrations have characteristics that are unique to an individual—characteristics such as the size of the heart chamber and the thickness of its walls, as well as variations within an individual due to dynamic changes in the heart's mechanical properties, such as transient increased stiffness of the ventricle. The unique characteristics of a person's heart sounds, for example, characteristics of the time-based waveforms representing such sounds, can be "fingerprinted", or captured, by a variety of measurements and parameters, and then used in a number of important ways.

If the hemodynamic condition of an individual, and of that individual's heart properties, remains constant, then one would expect that the associated heart-sound waveforms and the associated fingerprint(s) would remain relatively constant. The acoustic waveforms and fingerprints for an individual that demonstrate change over time would indicate a change in the mechanical properties of the heart, and/or in the hemodynamic state of individual per se. For example, if an individual experiences a transitory ischemic condition that causes increased stiffness of the left ventricle, along with increased left ventricular end diastolic pressure, one would expect an abnormal heart sound, such as an S3 or S4 heart sound, to develop. Aside from noting a new development of abnormal heart sounds, changes in specific parameters can be useful when one is evaluating change in a person. As an illustration, the acoustic fingerprint could be used to quantitate the amplitude of the normal S1 heart sound during exercise, with the expectation that a healthy individual would display increased amplitude, with the lack of an increased amplitude being interpretable as a sign of disease.

Another area of interest involves quantitating changes that take place during the administration of drug therapy to a patient. To illustrate this, it is common to treat heart-failure patients with diuretics, and it would be expected that the acoustic fingerprint in a patient undergoing treatment with diuretics would change as the hemodynamic state of that person changed.

Beside the utility of employing such a fingerprint for tracking changes in the same individual, such a fingerprint could be used in a comparison with a "normal" fingerprint for a particular selected population. Thus, to assist in diagnosis of left ventricular dysfunction, the fingerprint of an individual with altered left ventricular mechanical properties could be compared to the fingerprint for a non-diseased population in the same age range, and the differences in these fingerprints could be used to assist in the diagnosis of the presence of left ventricular dysfunction.

The process of creating an acoustic fingerprint for an individual, generally speaking, consists of a acquiring a person's acoustic heart sound data (signature) along with ECG data (signature), processing the heart-sound data to detect particular waveform components, and then quantitating various parameters and measurements. A list of parameters and measurements that might make up a fingerprint include (a) durations of the various heart sounds, S1, S2, S3 and S4, (b) amplitudes of these heart sounds, (c) relative amplitudes of the same heart sounds, for example, S1/S4 ratio, (d) timing relationships among the heart sounds, for example the S4 to S1 heart sound interval, (e) timing relationships between heart sound components and ECG data, for example, Q onset to S1 interval, (f) frequency composition of heart sounds (i.e., energy plots of the whole acoustic waveform or of any of its sub-components), (g) presence of abnormal heart sounds, including the presence of murmurs and stenosis, (h) multi-parameter "spaces", such as the relationship of PR interval to S4 interval, and many more.

The detailed description of the invention which now shortly follows will more fully amplify these various considerations and advantages associated with acquiring and correlating acoustic and electrical heart signatures. It will also disclose other features and advantages of the invention in categories which will become quite clear to those generally skilled in this art.

DESCRIPTION OF THE DRAWINGS

FIG. 8 is an illustration of one very useful form of an output report, generally taking the form of a strip chart, which includes both graphical, pictorial and text information, based upon practice of the present invention.

DETAILED DESCRIPTION OF THE INVENTION

Figure 1:
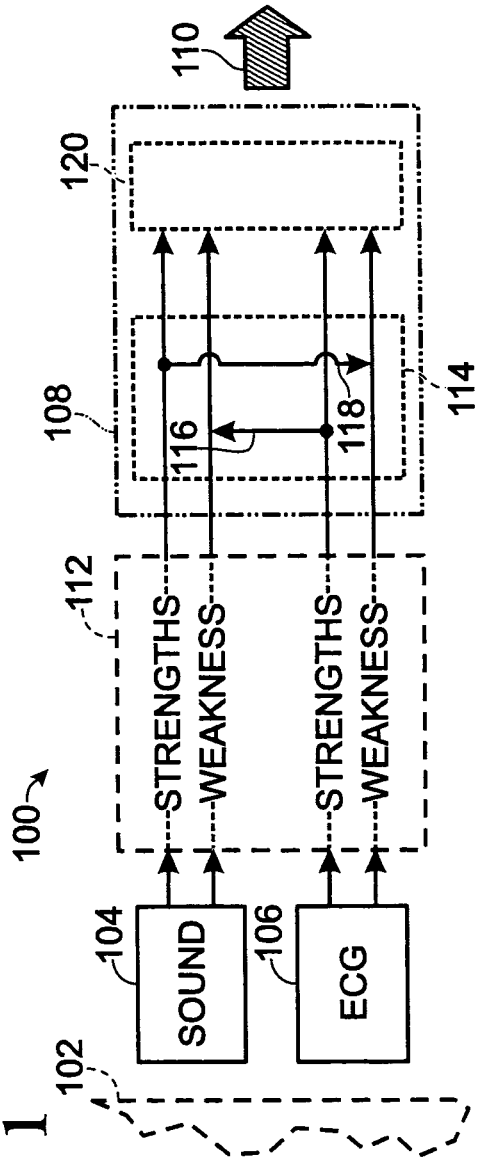
FIG. 1 is a high-level, stylized and schematic/block diagram generally illustrating one view of the architecture of the present invention, and in particular, demonstrating graphically the cross-correlation uses of strengths of ECG and sound signature information derived from a patient to buttress, so-to-speak, weaknesses in the other one of these two different kinds of data.
Figure 2:
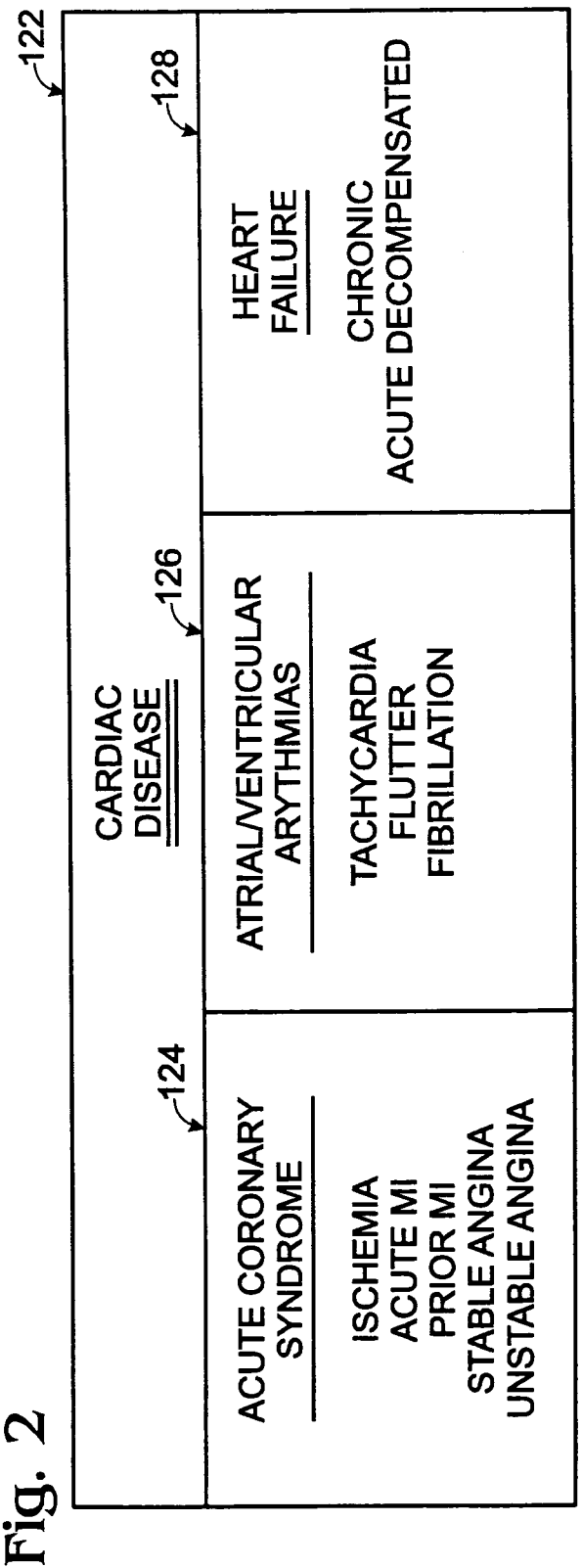
FIG. 2 illustrates, in a fully labeled block, a representative and important list of cardiac disease conditions that are made especially identifiable in accordance with practice and use of the present invention.

Turning attention now to the drawings, and beginning with FIGS. 1 and 2, indicated generally at 100 in FIG. 1 is a high-level overall view of one way of visualizing the structure and methodology of the present invention. This point of view, as is true with respect to all of the other system and methodology illustrations herein, pictures a preferred and best mode embodiment of and manner of practicing the present invention.

System and methodology 100 are designed, in accordance with the present invention, for monitoring and characterizing a person's heart condition for various medically related purposes, and in FIG. 1, a person, or a subject, is illustrated very schematically in dashed lines at 102. As will now become more fully apparent, the system and methodology of this invention enables and accomplishes monitoring and characterizing of heart condition through steps including (a) acquiring what is referred to herein as a subject's acoustic heart signature, (b) additionally acquiring, substantially simultaneously, available electrical heart-signature information from that same subject, (c) choosing various selectable elements of determined interest contained in these two signatures, and relating the same in several different manners, (d) thereafter employing relationship results, which are time-dependent results, to create a heart-condition "fingerprint", and (e) utilizing such a created fingerprint for various purposes, such as to create an output report in printed and/or electronic form, to effect control over some suitable form of medically-related interaction with the subject, such as implementing control over the operation of an installed pacemaker, and (f), among other things, enabling a comparison of a current fingerprint either with a prior-obtained fingerprint from the same subject, or a comparison of a current fingerprint with a database from a particular population of people containing relevant fingerprint information. Preferably, many of the steps of the invention are performed utilizing a suitably programmed digital computer.

Accordingly, illustrated at 104, 106, respectively, in FIG. 1 are suitable sound, or acoustic, and ECG, respectively, sensors which are appropriately "coupled" non-invasively (as pictured in FIG. 1) with respect to subject 102. These sensors are appropriately connected to feed information to an appropriately programmed digital computer 108, also referred to herein as processing structure, wherein various inter- and cross-relating processing steps, shortly to be described, are performed for the purpose of producing different categories of output, or output information, represented in FIG. 1 by a large and broad shaded arrow 110.

Sensors 104, 106 are referred to herein also, respectively, as acoustic and electrical data-gathering devices including, in each case, appropriate data-gathering structure, such as a microphone for device 104, and an electrode for device 106. As was mentioned above, in the illustration presented in FIG. 1, and preferably in relation to practice of the present invention, sound and ECG electrical data, or signatures, are gathered non-invasively, though, as will be explained a bit later herein, invasive data-gathering practices may also be employed if deemed desirable and/or necessary. While different specific devices may be employed for sensors 104, 106, a very practical unified device designed to capture both sound and ECG signature information is described in currently co-pending U.S. patent application Ser. No. 10/389,402, covering an invention entitled "Method and Apparatus for Detecting and Transmitting Electrical and Related Audio Signals from a Single, Common Anatomical Site", filed Mar. 14, 2003, and currently accessible as U.S. Patent Application Publication No. 2003-0176800-A1, published Sep. 18, 2003. For the purpose of useful background information herein, and inasmuch as we believe that this kind of a device offers a practical and very useful manner for gathering acoustical and ECG electrical data, all of the disclosure contents of that currently pending and now published U.S. Patent Application are hereby incorporated herein by reference.

As has already been mentioned herein, the acoustic and electrical heart signatures which are gathered for use in accordance with practice of the present invention, are time-based in nature, and collecting these signatures utilizing a device such as the one illustrated and described in the just-referred-to co-pending U.S. Patent Application provides a very convenient way for collecting these signatures effectively from a common anatomical site, and doing so simultaneously. Sensors 104, 106, in whatever form, and as illustrated in FIG. 1, are deemed to be appropriately positioned relative to subject 102 to collect the desired acoustic and electrical signatures.

A dashed block 112 in FIG. 1 is provided in this figure along with pairs of "arrow-headed output lines" coming from sensors 104, 106, to emphasize our recognition of the earlier characterized strengths and weaknesses which are associated with each of the two categories of signatures, acoustic and electrical, with respect to the ready ability to discern in each, and from each, certain aspects of human heart behavior. One of the important features of the present invention is that processing performed by computer 108 effectively utilizes the cross-complementary strengths of each to buttress the weaknesses of the other. This concept is illustrated schematically within the block which represents computer 108 in FIG. 1 by a dashed-line sub-block 114, wherein two, oppositely pointing, arrow-headed lines 116, 118 symbolize, respectively, use of the strengths of the ECG signature to buttress weaknesses in the acoustic signature, and use of the strengths of the acoustic signature to buttress the weaknesses of the ECG signature.

Another dashed-line sub-block 120 pictured within the block representing computer 108 represents structure and software within programmed computer 108 for performing various steps of signature processing and correlation in accordance with practice of the invention.

While those skilled in the art, in the context of practicing the present invention, may well discern other heart conditions which can be helpfully recognized and identified for characterization, and other purposes in accordance with practice of this invention, block 122 in FIG. 2 illustrates principal members of the well-recognized families in different categories of cardiac disease with respect to which use of the present invention has been found to be particularly helpful. The three principal illustrated "families" under the general heading "CARDIAC DISEASE", include "ACUTE CORONARY SYNDROME" (ACS) 124, "ATRIAL/VENTRICULAR ARRYTHMIAS" 126, and "HEART FAILURE" 128.

In family 124 in FIG. 2, illustrated specifically under the category ACS, are ISCHEMIA, ACUTE MYOCARDIAL INFARCTION (AMI), PRIOR MYOCARDIAL INFARCTION (PMI), STABLE ANGINA and UNSTABLE ANGINA. Under the category ATRIALNENTRICULAR ARRHYTHMIAS, listed are TACHYCARDIA, FLUTTER and FIBRILLATION. Listed under HEART FAILURE are both CHRONIC and ACUTE DECOMPENSATED HEART FAILURE.

Not specifically set forth in the table of FIG. 2 are the other cardiac disease conditions respecting which, as suggested above, the fingerprinting practice of this invention has utility. Included among these is a cardiac disease category referred to as Dysfunction with a number of manifestations, one of which is known as Enlargement. Also not specifically listed in block 122, but readily accessible via practice of the present invention, is information relating to Murmurs, and systolic and diastolic Dysfunction, as well as other conditions.

Figure 3:
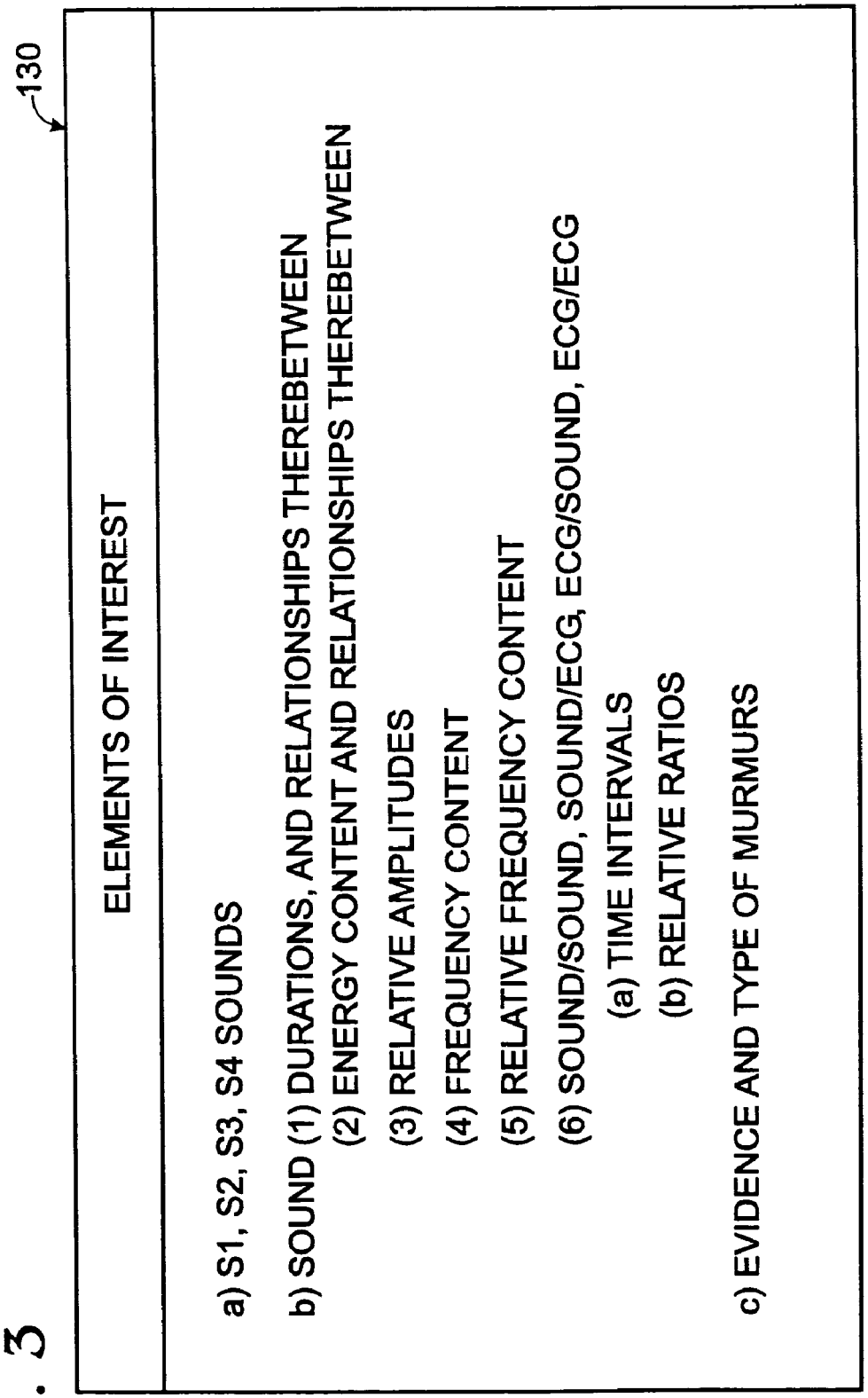
FIG. 3 also illustrates, in a fully labeled block, matters referred to herein as elements of interest which may be selected/chosen from gathered acoustic and electrical heart signatures for the purpose of performing very useful processing and cross-correlation to reveal and characterize heart conditions like those set forth in FIG. 2.

Turning attention now to FIG. 3 in the drawings, here, in a block shown at 130, are so-called "ELEMENTS OF INTEREST" which are elements selectable from the acoustic and electrical gathered heart signatures deemed to be especially useful in monitoring and characterizing heart condition as a result of appropriate signal processing and various acts of data correlation. Within these elements of interest, three broad categories are pictured generally in FIG. 3 labeled (a), (b) and (c). The first mentioned category of elements includes the well known S1, S2, S3 and S4 heart sounds. Within category (b), the second category, elements here include various aspects of and relationships between different sounds, and these various aspects and cross-relationships are clearly listed within block 130. The third category relates to evidence of and types of murmurs.

Figure 4:
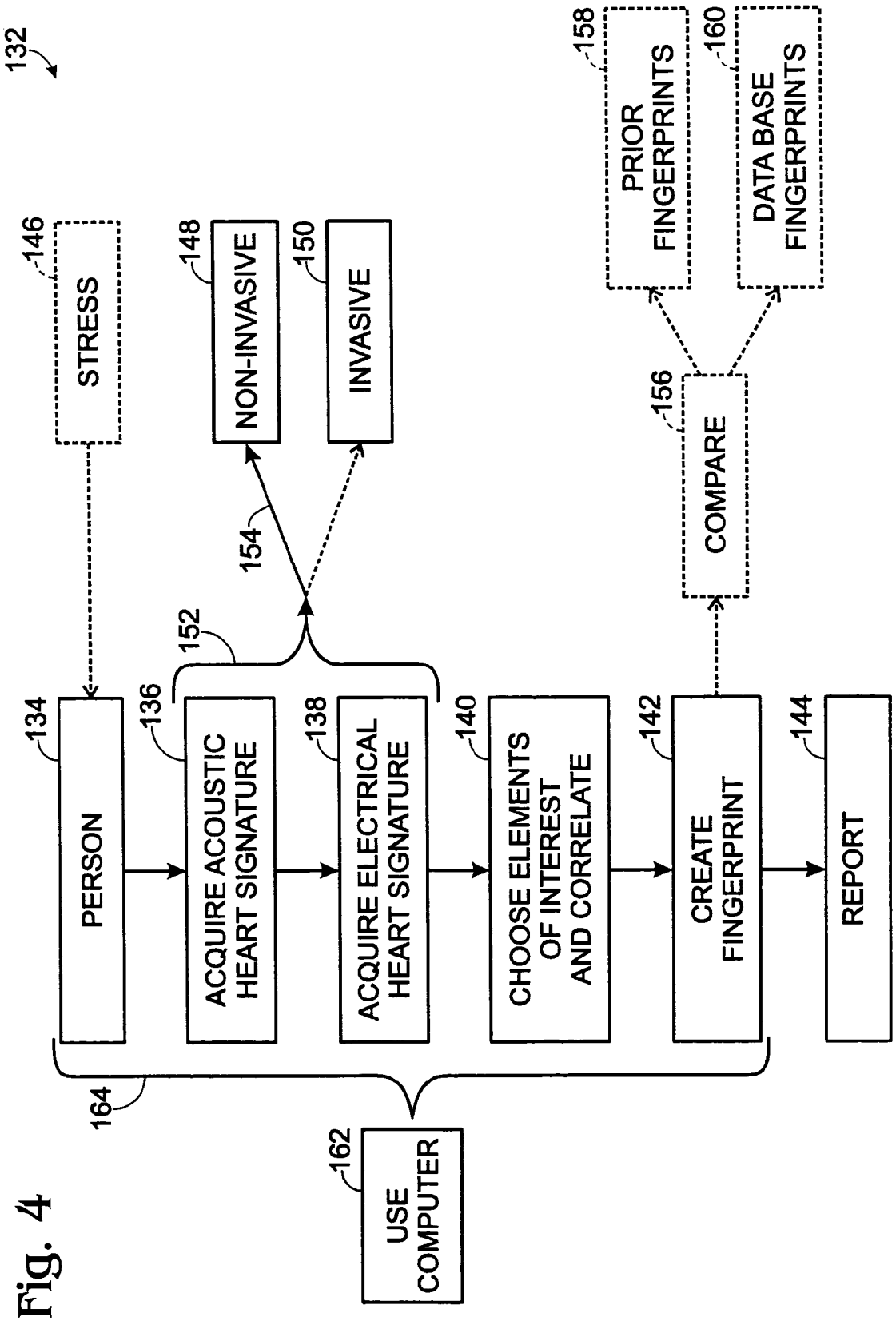
FIG. 4 is a block/schematic diagram, presented in a manner which is more detailed than the presentation provided in FIG. 1, further illustrating the methodologic and structural architecture of the present invention.

Turning attention now to FIG. 4 in the drawings which shows another block/schematic representation of the structural and methodologic architecture of the present invention, the overall arrangement pictured in FIG. 4 is generally designated 132. Included within the arrangement pictured at 132 are a block 134 representing a subject or a person, a block 136 representing the step of acquiring a subject's acoustic heart signature, a block 138 representing the step of acquiring of a subject's electrical heart signature, a block 40 representing steps involving the choosing of elements of interest, and the subsequent processing steps involving those elements, including steps of correlation, a block 142 which represents the step of creating an appropriate fingerprint, and a block 144 which represents a suitable output activity, such as the creation of a report in printed and/or electrical form.

A dashed block 146 represents the practice, where desired, of subjecting a subject 134 to various kinds of stress conditions to assess the effect of such conditions on acoustic and electrical signatures. Blocks 148, 150, along with bracket 152 and an arrow-headed line 154, collectively represent the selectable opportunity for the gathering of heart-signature data selectively either non-invasively or invasively.

A dashed block 156 represents the opportunity to employ a created fingerprint for the purpose of comparing it either with a prior fingerprint (dashed block 158) acquired earlier from the same subject 134, or of comparing it with a database (dashed block 160) of similar fingerprints acquired from a particular selected population of other subjects.

A block 162, associated with a broad, upright bracket 164, represents use of a computer, such as previously mentioned computer 108, to perform various data-acquisition and signal-processing and correlating steps which are performed in accordance with practice and use of the present invention.

Figure 5:
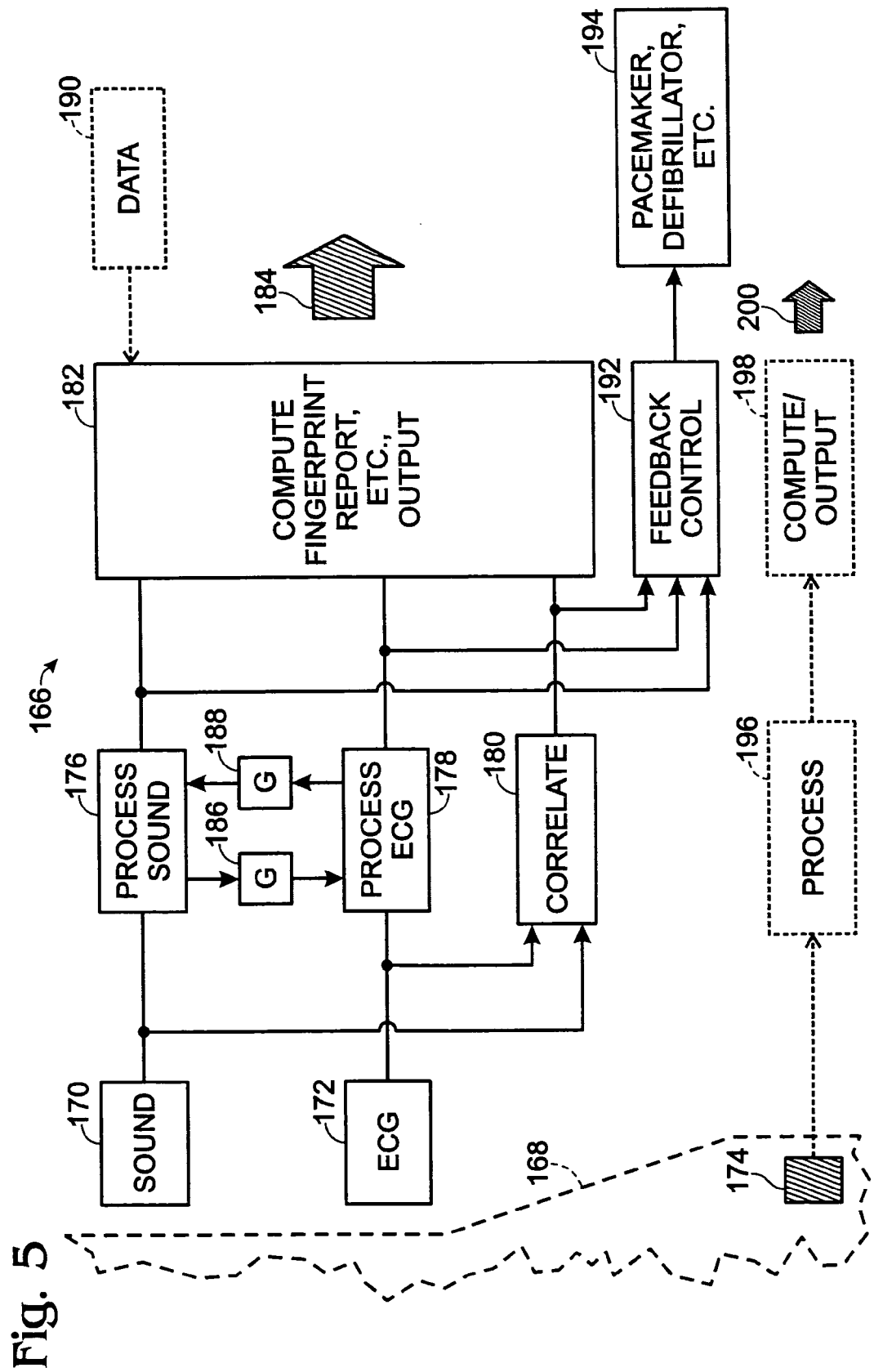
FIG. 5 provides another block/schematic diagram illustrating the structure and methodology of the present invention.

Shifting attention now to FIG. 5 which illustrates yet a further manner of viewing certain aspects of the structure and methodology of the present invention, here an organization now to be described is shown generally at 166 in this figure.

The fragmentary, dashed-line shape shown on the left side of FIG. 5 as 168 represents a subject from whom signature data is to be gathered, and gatheringly associated so-to-speak, with this subject are a noninvasive sound sensor 170, a noninvasive ECG electrical sensor 172, and a source 174 of invasively gathered data of any appropriate category, such as the category of pacemaker operational data.

Within the "computer world" associated with what is shown at 166 in FIG. 5 are a specific sound processing block 176, a specific ECG electrical-signal processing block 178, a correlation processing block 180, and a computational and outputting processing block 182 which bears responsibility for computation of a fingerprint, and for producing a report, or other form of output (broad shaded arrow 184) like previously mentioned output 110 seen in FIG. 1.

Two small blocks 186, 188, each marked with the capital letter "G", are connectively interposed blocks 176, 178 to represent data-acquisition gain advantages which relate to the previously mentioned practice of the present invention to use the strengths of one of the two categories of gathered signature data to buttress the weaknesses of the other category of data. Here, the concept of "gain" provides simply one way of visualizing the opportunity for cross-employing such signature strengths.

A dashed block 190 shown at the upper right corner of FIG. 5 represents, collectively, blocks 156, 158 and 160 in FIG. 4 that relate to various kinds of data comparison (serial or otherwise) that may be performed with respect to a computed signature fingerprint.

Further illustrated in FIG. 5 are a block 192 labeled "FEEDBACK CONTROL" and a block 194 labeled "PACEMAKER, DEFIBRILLATOR, ETC.". Feedback control block 192 draws information effectively from processed sound information, processed ECG information, and processed correlation information, to enable the use thereof to supply feedback control for various selectable medically relevant purposes, such as for modifying, adjusting, etc., devices such as a pacemaker, a defibrillator, and other. Those skilled in the art will readily understand how such feedback information may be designed to accomplish this kind of control environment.

Finally illustrated in FIG. 5 are two dashed-line blocks 196, 198 which are associated with a broad, shaded arrow 200. Blocks 196, 198 are connectively associated with invasive device 174, with block 196 being coupled to process invasively-output information from device 174 for the purpose of feeding information to block 198, which preferably forms a portion of previously mentioned computer 108, for the ultimate purpose of furnishing additional output and/or feedback control information represented by arrow 200. Here also, those generally skilled in the art will understand how information from an invasive device, such as device 174, can be so employed to advantage.

Specific and Various Illustrations of, and Discussions and Exploratory Comments About, Fingerprinting Beginning this illustrative discussion of fingerprinting with a brief reminder about, and a certain amount of elaboration relative to, aspects of the two modalities (ECG and PCG) of signatures which are gathered and processed in accordance with this invention, while each modality on its own has a particular strength in carrying information useful for the identification of acute, high risk cardiac conditions, both modalities and their information content have limitations with respect to their sensitivity and specificity for diagnostic and prognostic purposes in cardiograph and/or monitoring/trending applications.

In particular, the ECG signature carries information about acute and non-acute ischemia due to coronary artery disease that leads to damaged heart tissue, ranging in severity from mild ischemia to life threatening myocardial infarction or sudden cardiac death. The evidence in the ECG signature, for example, for ACS depends on the size of the damaged heart muscle area, its position with respect to the electrical vector that the ECG signature can detect, and the time of ECG recording in the acute process. Other defects in the heart's electrical conduction system can create similar, confounding changes in the ECG signal which limits the ability of the ECG signature to point out unambiguously structural defects induced via ACS. With respect to the diagnosis of congestive heart failure (CHF), the ECG signature basically does not provide diagnostic information at all.

The PCG acoustic signature carries diagnostic information about ACS and CHF through the presence and characteristics of heart sounds, which are highly sensitive to pathologic changes of hemodynamic properties of the cardiovascular system. In particular, the presence of diastolic heart sounds S3 and/or S4 points out that the heart underwent pathologic hemodynamic changes and is having difficulty performing its function as intended. The root cause for those hemodynamic changes can be manifold, and the heart sound information has to be evaluated in the clinical context the patient presents for diagnostic evaluation.

The PCG signature reflects mainly hemodynamic and mechanical properties of the heart, while the ECG signature contains more information about the conduction of electrical signals. Therefore, the PCG and the ECG informations are mostly orthogonal in nature, and the appropriate combination of diagnostic information from PCG and ECG signals will enhance the sensitivity and accuracy of the computerized evaluation of both signals for diagnostic cardiographic and/or monitoring purposes. The combination of PCG and ECG evaluation can be done by either the combination of the diagnostic output of separate PCG and ECG algorithms, as well as by the creation of new diagnostic measurements composed of inter-PCG/ECG timing intervals and/or morphology characteristic, and/or the combination of new diagnostic measurements (see Table 1 below). The way the combination of PCG and ECG information can happen ranges from simple linear algebraic equations up to using sophisticated knowledge based systems and neural networks.

TABLE 1

Example for the different options to combine ECG and heart-sound information to enhance the diagnostic capability for cardiac diseases in cardiographs and/or monitors.

|  | Combine diagnostic findings from separate ECG and PCG analysis | Adjust gain/thresholds depending on diagnostic findings in the PCG or ECG signal | Creation of inter-PCG/ECG Mxs | Combine ECG, PCG and/or multiple inter-PCG/ECG Mxs |
|---|---|---|---|---|
| Cardiac Disease (example) | Ischemia | Ischemia | CHF | CHF |
| ECG algorithm alone | ST elevation above threshold | ST elevation below threshold | — | Heart Rate |
| Sound algorithm alone | S4 present | S4 present | — | S3 strength, S1 pitch |
| ECG/Sound Mx | — | — | Q-S1 | Q-S1 |
| COR | Ischemia index = S4 strength × ST elevation | S4 detected, lower threshold for ST elevation in ECG algorithm & reanalyze. If ST elevation higher than new threshold, make Ischemia call | CHF present if Q-S1 > xx ms | CHF index = (S1 pitch/HR)*S3 strength * Q-S1 |
| Diagnostic enhancement | Specificity: Presence of ST elevation underlines that the S4 is due to Ischemia versus other chronic structural heart diseases | Sensitivity | Sensitivity: Inter-PCG/ECG Mx offers additional information not available in ECG or PCG alone. | Sensitivity/Specificity |

Considering, now, various illustrations of fingerprinting, and to insure a common understanding, the following phrases will be explained:

Extended measurements: This term refers to the collection of additional parameters that could be generated to quantitate heart sounds and their relationship to the ECG. Examples include time intervals, energy content or relative ratios, and frequency content. Extended measurements will be used to create a "fingerprint", assist in diagnosis, or be used to produce expanded statements (such as risk or prognosis), or additional statements (such as left ventricular dysfunction).

Fingerprint: An ECG/sound fingerprint is intended to provide a collection of extended measurements that quantitatively describe the heart sounds and/or ECG that can be used to document the characteristics of a single ECG and heart sounds recording, or to assess change within a single subject. The specific extended measurements included in the fingerprint will depend on many considerations including the ability of the measurements to assist in diagnosis/prognosis, or to track change.

Extended Measurements: There are many extended measurements that are considered. These fall into several basic categories:

Intervals: While there are many intervals that will be assessed, the following appear to have the most potential. Many of these may need to be indexed or normalized for heart rate or PR interval:

P onset in ECG to S4: There is previous literature that suggests that P onset to S4 timing changes over the course of AMI and is related to left ventricular end diastolic pressure (LVEDP);

Q onset in EGC to S1 (electromechanical delay): This measurement is affected by conduction abnormalities and disease;

Q onset to S2 (electromechanical systole): This interval is also affected by conduction abnormalities and disease;

S4 to S1: A timing relationship that should be important for audibility in relation to detecting increased LVEDP;

S2 to S3: Another timing relationship that should be important for audibility;

R to R: Heart rate variability is a well-known ECG parameter.

Relative Amplitudes: Several researchers and the literature suggest that relative amplitude of various heart sounds provide information:

S1 to S2: The audible relationship between S1 and S2 intensity is used in auscultation for detection of ventricular tachycardia versus supraventricular tachycardia;

S4 to S1: This parameter should relate to audibility, and might contain other information, such as severity of ischemia;

S2 to S3: This parameter should relate to audibility as well, and might contain other information.

Relative Frequency Content: There is little information concerning the importance of relative frequency content of the various heart sounds, but this parameter should help define audibility of S3/S4. Higher LVEDP would create greater tension in the walls and might produce higher frequency content:

S4 to S1 and S2 to S3: At a minimum for determination of audibility;

S3 to S4: No reference in the literature, but might determine relative audibility of each and relationship to LV (left ventricular) pressures.

Relative Energy Content: Energy content would combine contributions of amplitude and frequency. The exact definition of this is yet unclear, but is likely a parameter measured in the frequency domain. There may be overlap with relative frequency content:

S1 to S2, S4 to S1, S2 to S3, S3 to S4: The relationship of these in normal and diseased states will need investigation.

Frequency Content: The frequency content of the heart sounds can be determined in the frequency domain:

Within the S4 window: Currently done to insure that the S4 sound is not due to noise, or other disturbance, but might also relate to degree of increased LVEDP or loss of compliance;

Within the S3 window: Currently done to insure that the S3 sound is not due to noise or other disturbance, or to detect additional heart sounds such as pericardial knock, but might also relate to loss of compliance;

Related to the S1: Needs to be developed; predicted to relate to contractile function of the left ventricle (LV) and/or LV pressure;

Related to the S2: Needs to be developed; predicted to relate to function of the LV and/or LV pressure.

Change in Presence/Absence or amplitude/energy of S3/S4: This is not possible in a single 10-second recording, but is useful in a monitoring application.

Murmurs: For detection of systolic or diastolic murmurs and their shapes and types, and not intended to specify cause of murmur.

Pseudo-Apexcardiogram: Low-pass filtering of an acoustic produces a signal equivalent to previous apexocardiogram signals. Apexocardiograms have been reported extensively in the literature and have been used primarily to illustrate the pressure signal, and quantitate the atrial or a-wave component.

Respiratory Sounds: Higher frequency sounds from the lungs are present in the acoustic signal. The information might be helpfull in differential diagnosis of shortness of breath due to cardiac or respiratory causes.

Miscellaneous: The following areas are also being considered, some without support in the literature:

Heart Rate (HR): High heart rate at rest is an ominous sign since it reflects compensatory activity of the autonomic nervous system. Patients with heart failure (HF) compensate for a low stroke volume by increasing their heart rates.

Therefore, and S3 or S4 in a patient with a relatively high heart rate probably reflects more significant disease than a patient with a more normal HR. Medication affects HR and will need to be taken into account.

Duration of S3/S4: A longer duration sound might indicate a different pathology than a shorter duration.

Contour of sound: This is known to be significant for murmurs, and might be important for S3 and S4 since a sound that begins abruptly might be differentiated from one that begins more gradually or blends with the S1/S2.

As we continue to explore the possibilities of use of the present invention, the following discussions, including references to the relevant literature, reveal the exploratory power and utility promise of the present invention in relation to selecting, processing and correlating certain elements of interest in gathered acoustical and electrical signatures.

Intervals

P onset to S4:

Summary: It has been proposed that the earlier an S4 is generated after atrial contraction (onset of P-wave) the more pathological the condition. P onset timing to S4 has been studied in patients with AMI and in relation to LV pressure. It was shown P onset to S4 is smaller with higher LVEDP during the acute phase of AMI and then resolve during recovery in patients with better prognosis. The PR interval can be used to normalize the interval for various PR durations. The P onset to S4 interval could be used in the following ways:

1. To distinguish more benign S4's from those more pathological (or S4's related to elevated LVEDP);
2. To assist in diagnosis of AMI and ischemia (ST changes not meeting current threshold criteria but in the presence of an S4);
3. To categorize prognosis with AMI (in a snapshot or by comparing the interval over the course of the MI);
4. To determine severity of AMI/MI/LVH as it indicates higher LV pressures;
5. In a monitoring application, to track change in LV pressures or onset of ischemic events.

Literature Summary: Twenty patients with S4 and AMI were studied. The interval from P onset to S4 was measured by hand on paper traces and given as a percentage of the PR interval. The interval increased from 81% on the first day to 89% on the fourth day, demonstrating that with resolution of the infarct the atrial sound moved towards the S1 (diagnosis). Those patients with a complicated recovery had an earlier S4 than those whose recovery was uncomplicated (prognosis). There was a significant correlation between the ratio and pulmonary artery diastolic pressure (indicating shortest ratios meant greatest LV dysfunction) (severity). Bennett et al, Proceedings of the British Cardiac Society.

Simultaneous hand measurement on paper recordings of P onset to S4 inadvertently determined LVEDP in nineteen patients with coronary artery disease (CAD) studied before and after atrial pacing. Thirteen patients developed angina and significant rise in LVEDP and a consistent decrease in P-S4 interval. The six patients who had atrial pacing without angina had no change in LVEDP or P-S4 interval. The resting data showed an inverse correlation between LVEDP and P-S4. In addition, the P-S4 discriminated patients with normal and abnormal LVEDP>15 mm-Hg.

The P-S4 intervals can be divided into three zones:

1) <=130-msec, usually associated with abnormal LVEDP;
2) >130-msec, but<140-msec, cannot clearly discriminate LVEDP;
3) >=140-msec, usually associated with normal LVEDP;

The table below shows measurements before and after atrial pacing to induce angina. It is possible that the P-S4 interval may not be applicable either to patients with extremely early diastolic P-waves, very short or prolonged PR intervals, or distorted P-waves caused by interatrial conduction defects.

|  | LVEDP | | P-S4 msec | | PR int msec | | HR | |
| --- | --- | --- | --- | --- | --- | --- | --- | --- |
|  | Before | After | Before | After | Before | After | Before | After |
| Mean | 16.1 | 25.8 | 135.3 | 113.8 | 155.8 | 157.5 | 76.8 | 77.4 |
| StDev | 9.3 | 11.5 | 21.9 | 24.3 | 25.3 | 24.6 | 10.0 | 10.2 |

From Schapira et al, British Heart Journal.

Electromechanical Systole (Q onset to S2):

Summary: There has been much published about the Q onset to S2 interval (or electromechanical systole). To determine the interval, the subject must have normal QRS durations (meaning not wide complex tachycardias, for example) and ectopic beats should not be used to create an average value. The Q onset to S2 interval approximates isovolumic contraction time plus ejection time. Gender corrections have been proposed and normalizing using heart rate is necessary. The interval is known to be affected by medications, in particular, by positive inotropic drugs. It has been shown that QS2 is shortened in AMI due to shortening of ejection time. One researcher has stated that a short QS2 in a patient with chest pain indicates ischemic disease. Studies have shown that in a patient with AMI, the shortened QS2 lengthens during recovery and that the shorter the QS2 the more LV dysfunction present. Two studies did not find shortening of the QS2 with AMI.

A study in HF has shown QS2 to be longer than in normals. Illustrative uses for QS2 would be:

1. To assist in diagnosis of AMI and ischemia (by shortened QS2 interval);
2. To categorize prognosis with AMI (in a snapshot or by comparing the interval over the course of the MI);
3. To assist in diagnosis of HF (by lengthened QS2 interval);
4. To evaluate change in HF or ischemic condition, or recovery from AMI.

Literature Summary: For all studies, the researchers only included subjects with normals QRS durations (normal conduction patterns). One hundred controls and twenty patients with AMI were studied during held expiration and supine. The Q onset to S2 interval was shortened in all twenty AMI patients as compared to the controls. In normals measurements were taken before and after exercise to see relationship to HR. This shortening tended to return towards the normal range during the three week recovery period. This, perhaps, could be used to age infarcts.

Fifty patients with AMI were studied serially. The value for Q onset to S2 was outside the normal range for 80% of the patients. The shorter the interval the more severe the LV dysfunction. Heikkila et al, Circulation.

QS2 was measured in twenty-four supine patients with AMI studied by cardiac catheterization within the first twenty-four hours of onset of symptoms. The twenty-four patients were divided into two groups—with (Group-2) and without (Group-1) LV failure. Forty-two normals were also studied (age 25 to 75). The regression equation for the normals was QS2=−0.0020×HR+0.522.

|  | QS2 | LVEDP |
|---|---|---|
| Group 1 | 0.352 +/− 0.013 | 14.68 +/− 4.56 |
| Group 2 | 0.345 +/− 0.040 | 26.96 +/− 8.28 |
| Both groups | 0.345 +/− 0.040 | 21.09 +/− 9.11 |

QS2 was generally shortened in AMI as compared to normals, but between the two groups there was not a significant difference. Hamosh et al, Circulation.

Twenty patients with AMI were studied. QS2 in patients with an uncomplicated course was 27.0+/−3.6-ms, and 52.0+/−4.7-ms in patients with a complicated course. Patients with the highest pulmonary artery diastolic pressure tended to have the shortest QS2 intervals. Bennett et al, Medical Research Society.

Samson studied thirty-one patients with AMI that were grouped according to the absence (Group-1, fifteen patients) or presence (Group-2, sixteen patients) of radiological pulmonary edema and major arrhythmias. Values for normals were those published by Weissler in 1968. In each patient the QS2 interval and the ejection time were abnormally shortened at some stage, usually during the acute phase. Values were compared at maximal shortening, at discharge and at follow-up. The Group-2 patients tended to shorten the QS2 by mean of 31-msec or more, and maximum value of 51-msec or more. The shortening of the QS2 was predominantly due to shortening of the ejection time and the patients with worse disease tended to shorten the QS2 more than those with lesser disease. Samson, British Heart Journal, 1970.

Twenty normals and sixteen patients with untreated HF were studied. QS2 was indexed using regression equations developed by Weissler.

The range of QS2 indexed in normals was 521-to 551-msec. Wertheimer, Acute Cardiac Problems.

Two hundred and eleven normals and twenty-seven subjects with heart failure were studied, resulting in the following:

|  | QS2 | S1–S2 | QS1 |
|---|---|---|---|
| Normal male | −0.0021 HR + 0.546 SD 0.014 | −0.0018 HR + 0.456 SD 0.015 | −0.0004 HR + 0.090 SD 0.011 |
| Normal female | −0.0020 HR + 0.549 SD 0.014 | −0.016 + 0.461 SD 0.012 | −0.0003 HR + 0.089 SD 0.009 |
| HF | Mean 371.0 SD 6.0 | Mean 293 SD 7.1 | Mean 82 SD 2.5 |

The patients with HF had long pre-ejection periods, short LV ejection times, and normal QS2 intervals. The pre-ejection period was longer due to longer QS1 and isovolumic contraction interval. In normals, QS2 is longer in females than in males, but QS1 is similar in males and females. The longer QS1 in HF could reflect an increased electromechanical delay or a reduced rate of LV pressure rise prior to S1. Weissler et al, Circulation, 1968.

Fifteen AMI patients were studied within three days of onset of symptoms but while pain free. Patients with LBBB (left bundle branch block) were excluded. Weissler studied two hundred and eleven normals and developed the following regression equations:

$QS1$ index=$QS1$+0.4×$HR$-msec (men and women)

$QS2$ index=$QS2$+2.1×$HR$-msec (men) and=$QS2$+2.0× $HR$ (women)

|  | QS1 Index | QS2 Index |
|---|---|---|
| First day | 88.7 +/− 11.5 | 519.9 +/− 28.8 |
| Second day | 91.3 +/− 10.7 | 517.4 +/− 21.6 |

Initial QS2 Index was shortened in the AMI group compared to those seen by Weissler in normals. Day to day changes in QS2 index for individual patients ranged from a fall of 51-msec to a rise of 22-msec. Mean QS1 index differed very little from the expected normal values of 90-msec for men and 89-msec for women.

Fifty-one patients with AMI, forty patients without heart disease, twenty-three patients with chest pain without AMI, and sixteen patients with angiographically proven CAD were studied. Serial measurements were taken in the AMI group. QS2 in the AMI group was significantly shortened until the fourth week of hospitalization.

There was a significant correlation between the QS2 and HR in all groups. The regression equation for the normal group was QS2=−2.33×HR+548. An indexed QS2 was calculated as:

$$QS2\ index = 2.33 \times HR + QS2$$

| | Normals | AMI | Chest pain | Stable CAD |
|---|---|---|---|---|
| QS2 index | 550.2 +/− 3.3 | 538.3 +/− 3.2 | 529.3 +/− 5.6 | 570.0 +/− 3.2 |

Serial measurements of QS2 index indicated that the average value for the AMI group paralleled the LV ejection time index, being significantly low until the fourth hospital week. The lowest value was reached on day six with a gradual return to normal during the fourth hospital week. Hodges et al, Circulation.

Fifty patients with AMI were studied within twenty-four hours of the onset of symptoms. These were divided into three groups—Group-1, uncomplicated MI; Group-2, moderately extensive infarction; and Group-3, severe infarction. Electromechanical systole (QS2) and mechanical systole (S1 to S2) were measured. These were indexed to the standard HR of 70-bpm using:

$$QS2\ index = 546 - 2.1 \times HR +/- 14 SD$$

$$S1S2\ index = 456 - 1.8 \times HR +/- 15 SD$$

The values for QS2 were outside the normal range in 80% of the patients, and for S1S2, 82% were outside the normal range. The greatest deviation from normal was on the fifth day. Group-3 with severe infarcts had QS2 initially much shorter than the other groups and this group had worse prognosis.

| Time | Group | N | QS2 | S1–S2 |
|---|---|---|---|---|
| 1st day | All patients | 50 | 379 +/− 19 | 316 +/− 27 |
| | % deviation of mean from normal values | | −4% | −4% |
| 5th day | All patients | 50 | 363 +/− 18 | 299 +/− 23 |
| | % deviation | | −9% | −9% |
| 20th day | All patients | 45 | 368 +/− 31 | 306 +/− 30 |
| | % deviation | | −8% | −7% |
| | Normal | | 399 +/− 14 | 330 +/− 15 |
| | SD in % of mean | | +/−3.5% | +/−4.5% |

Shortening of QS2 in AMI is in marked contrast to its normal duration in chronic heart failure. Heikkila et al, Circulation.

Researchers evaluated the duration of the phases of LV mechanical systole in healthy men ages 45 to 65 years. Overall they found no age relationship to the durations. The duration of QS2 is "close" to the sum of isovolumic contraction time and ejection time. The researchers found:

Isovolumic contraction time: 54+/−12 (range 35–100)

Ejection time: 278+/−30 (range 200–340)

From Luomanmaki and Heikkila, Annals of Clinical Research, 1969.

Lewis reported the following values:

| Gender | Equation | Normal Index (msec) | SD |
|---|---|---|---|
| Male | QS2I = 2.1 HR + QS2 | 546 | 14 |
| Female | QS2I = 2.0 HR + QS2 | 549 | 14 |

Left bundle branch block and aortic valve disease decrease QS2, whereas positive inotropic agents decrease QS2. The authors state that QS2 tends to remain unchanged from normal even in disease states, unless drug effects are present although they note the shortening of QS2 with AMI as a result of increased adrenergic tone. QS2 can be used to assess the presence of positive inotropic drugs. A QS2I of less than 515-msec in a patient with chest pain strongly suggests ischemic disease—and another study suggested that patients with shortened values of QS2I have the most undeveloped collaterals. Lewis et al, Circulation, 1977.

Electromechanical Delay (Q onset to S1):

Summary: This interval is believed to be related to myocardial contractility, and is affected by abnormal conduction. The measurement can only be used on subjects with normal conduction (no LBBB or v-pacing, in particular). There has been no gender adjustment recommended. No change in QS1 has been found with AMI. Shortening of QS1 in patients with mitral stenosis and hypertensive valvular disease has been shown. Long QS1 implied impairment of myocardial contractility and has been documented as a finding in elderly subjects with and without heart disease. Although, we have not yet found any manuscripts relating long QS1 to HF, it would be a likely finding. Expected uses of QS1 interval would be:

1. To assist in diagnosis of HF (by lengthened QS1 interval);

2. To evaluate change in myocardial contractility or HF condition;

3. To confirm Mortara calls of LBBB or v-pacing, or to detect ventricular rhythms.

Literature Summary: Electromechanical delay has been shown to be associated with mitral stenosis and hypertension. Eighteen normals, twenty-five patients with hypertensive valvular disease and ten patients with mitral stenosis were studied with sinus rhythm and no overt CHF.

| | QS1 | QS1 range | QRS | R to R |
|---|---|---|---|---|
| Normal | 0.055 +/− 0.010 | 0.03 to 0.070 | 0.075 +/− 0.007 | 0.81 +/− 0.12 |
| Hypertension | 0.070 +/− 0.009 | 0.05 to 0.085 | 0.090 +/− 0.007 | 0.80 +/− 0.14 |
| Mitral Stenosis | 0.080 +/− 0.010 | 0.065 to 0.10 | 0.080 +/− 0.010 | 0.80 +/− 0.11 |

| Study | QS1 (seconds) |
| --- | --- |
| Weiss and Joachim | 0.05–0.07 |
| Gerhartz | 0.061 |
| Bull | 0.04 |
| Fahr | 0.02–0.03 |
| Lewis | 0.011–0.039 |
| Battaerd | 0.02–0.065 |
| Kanner | 0.03 |
| Leblanc | 0.02–0.04 |
| Kelly | 0.04 |

Values for normals from various studies, from Weissler et al, Circulation.

Friedman studied three groups of subjects. Group-1 consisted of elderly patients with no evidence of heart disease; Group-2 consisted of elderly patients with heart disease but no evidence of congestion; and Group-3 consisted of a group of younger, healthy individuals. The timing and intensity of the S1 has been related to the power and rapidity of ventricular contraction (dP/dt) as well as diastolic tone of the myocardium. An increased QS1 would then indicate impairment of myocardial contractility.

| Group | Q-S1 |
| --- | --- |
| 17 elderly patients without heart disease | 0.075 +/− 0.002 |
| 23 elderly patients with heart disease | 0.075 +/− 0.002 |
| 18 normal controls | 0.055 +/− 0.002 |

Energy Content

Summary: It is believed that the intensity of S2 reflects isovolumic relaxation of the LV and the S1 to max dP/dt (isovolumic pressure). Also, the PR interval is very important for the intensity of S1. Systemic and pulmonary hypertension will affect S2 intensity. There are many references to alterations during auscultation of intensity of S1 and/or S2. Absolute values will be impacted by patient body position, sensor position, and body mass between heart and sensor. They are also affected by valvular and aortic disease. Aortic valvular disease decreases S2 and systemic hypertension can increase it. Significant mitral insufficiency decreases S1. The ratio of S1 to S2 may, therefore, be more useful for our purposes. Practical uses for S1/S2 energy content might include:

1. Diagnosis of AMI and possibly HF;
2. Prognosis of AMI patients;
3. Monitoring applications indicating change in LV function.

Literature Summary: S1 and S2 in AMI: Twenty-five patients with AMI and twenty-three controls were studied. Patients with AMI were found to have diminished S1's and S2's by auscultation. Measurable reductions of S1/S2 frequently occurred in the absence of S3 or abnormal lung sounds. The diminished S2 in MI reflects impaired isovolumic relaxation of the LV, and the S1 relates to max dP/dt (isovolumic pressure). During recovery from AMI, intensity of S2 increased in nineteen of twenty-five patients. "The results of this study indicate that the intensity of heart sounds at the chest wall in patients with normal valves and normal transmission of sound is measurably diminished in patients following MI". Stein et al, Chest, 1979.

Parmley studied fourteen patients with AMI, seven of which did not survive. He found that LVEDP did not discriminate those who survived from those who did not. He also found that max LV dP/dt (which is related to intensity of S1, see above) did separate survivors from non-survivors. Parmley et al, Circulation, 1972.

Intensity of heart sounds at the apex was reduced in patients with AMI and this was not due to age, BP, HR, PR interval, or skinfold difference. "An unexpected and significant finding in this series was the very much greater reduction in sound intensity in the group of patients whose myocardial infarcts involved the posterior wall of the heart." Price et al, British Heart Journal.

Experiments with invasively instrumented dogs have shown that the amplitude of the aortic component of the S2 is not directly related to aortic pressures, aortic to LV differential pressures, or to the derivative of these pressures at the time of the dichrotic notch. Only the peak rate of development of the aortic to LV differential pressure gradient (first derivative maximum) had a consistent relationship to aortic S2. Each animal served as their own control and change in S2 amplitude from the baseline was determined. S2 amplitude is roughly related to aortic pressure. So for a monitoring application, any change resulting in alteration of dP/dt of the differential pressure would be reflected in change of S2 amplitude. Kusukawa et al, 1965.

Luisada has reported that changes in the S2 are caused by shifting in position and changes in magnitude of the aortic or pulmonary component caused by changes in pressure or structural changes of the vascular walls. Amplitude of the S2 is proportional to the peak value of dP/dt of the pressure difference between vessel and ventricle. Increased pressure in the aorta or pulmonary artery usually results in a louder S2. Systemic hypertension would result in a larger aortic component and pulmonary hypertension results in a larger pulmonary component. Pulmonary hypertension (acute or chronic) causes a wide splitting of the S2. The S1 and S2 modify their timing and arrival of components with valvular defects. Reversed splitting may occur with MI, ischemia, CAD, LBBB, and cardiomyopathies. Reverse splitting occurs in 25% of healthy elderly subjects. Luisada, American Journal of Cardiology, 1971.

Experiments were done on fifty-one dogs by altering their hemodynamic state through medications and mechanic obstruction of the great vessels. LV pressures were obtained directly from catheters in the LV. Other researchers have found that the S1 amplitude correlated well with max dP/dt. This points to relationship of S1 amplitude to vigor of contraction. The S1 amplitude also related to rate of change in wall tension and quantitatively to the peak rate of change in wall tension. The right ventricle seemed to contribute very little to the S1. Sakamoto et al, Circulation, 1965.

Relative Amplitude

Summary: S1 to S2 ratio is more accepted as changing with AMI. We will need to understand other mechanisms for alteration of S1/S2. Uses of a relative amplitude measurement might include:

1. Diagnosis of AMI;
2. Prognosis of AMI patients;
3. Monitoring for change in LV function.

Literature Summary: S4 to S1: One hundred normal subjects (ages 1–88), and forty-two patients with either aortic stenosis, systemic hypertension or coronary heart disease were studied. A magnitude of ½ of S1 or a frequency of 30-Hz tended to indicate a pathological S4, and the combination of the two criteria considered highly significant for pathology. Patients with aortic stenosis had increase in amplitude of S4 but similar frequency. Patients with hypertension in middle age had greater magnitude while older patients had increased frequency. Patients with CHD had increased magnitude and frequency as compared to controls. Perez et al, Angiology.

S1 to S2: Auscultation during AMI—"The heart sounds are usually normal in patients with small infarcts, but in patients with large infarcts the S1 may be soft or indistinct and the S2 accentuated." Goldman and Braunwald, Primary Cardiology.

The intensity of heart sounds in normals did not change significantly during a 12-week average interval between measurements. Patients in the period immediately after infarction, in comparison, to normals, showed a lower amplitude and lower intensity of the S1 and S2. Reductions of the intensity of sound frequently were in the absence of an S3. During the course of recovery from AMI, S2 increased in amplitude. Reference to mitral disease and PR interval affecting intensity of S1, and S2 affected by aortic stenosis and aortic regurgitation. Stein et al, Chest.

Change in Presence/Absence or Relative Amplitude/Energy of S3/S4

Summary: The literature describes the sequence of hemodynamic, ECG and patient symptom changes associated with ischemia. An increase in LVEDP occurs and ECG changes happen after heart sounds appear, and patient symptoms are the last to happen if at all. Useful information would be the following:

1. Heart sounds should improve detection of ischemia;
2. Heart sounds should provide earlier detection of ischemia than ECG alone;
3. In a monitoring application, heart sounds and ECG should provide a time course of the ischemic event.

Literature Summary: Hemodynamic and ECG changes during Ischemia: The pattern of change seen during balloon occlusion has been reported in several studies and intended to explain what happens during ischemic events. The first significant increase in LVEDP was noted at 18+/−4-sec. There was a constant linear fall of dP/dt max over the first 15-sec of occlusion. DP/dt max tended to level off at 20-sec after occlusion and was accompanied with an increase in isovolumic contraction time. Peak negative dP/dt showed a rapid fall during the first seconds of occlusion. Reporting of angina symptoms was extremely variable. In general, angina occurred later than 25-sec after the onset of occlusion (mean 34+/−9-sec) and after the initial increase of LVEDP. The average reduction of EF was 36% +/−16% from the control value. Among the parameters of LV function, the variables of relaxation appear to be the most sensitive and precede the alteration of contractility parameters. The occurrence of events was reported to be:

Relaxation failure—2-secs post occlusion;
Contraction failure—5-secs post occlusion;
Filling pressure up—15-secs post occlusion;
ECG changes—19-secs post occlusion;
Angina—25-secs post occlusion.

This symptomless ischemia may be accompanied by dramatic signs of LV failure being entirely reversible after short transient coronary occlusion." Sigwart et al.

In an echo study of cath coronary artery occlusion, the authors observed that dysynergy began at 19+/−8-sec, transient ECG changes at a mean of 30+/−5-sec and angina at 39 +/−10-secs after occlusion. Each occlusion resulted in ECG changes and angina after the onset of LV wall motion changes. Hauser, et al, JACC, 1985.

Seven patients were studied before, during and after angina induced by atrial pacing. Mean LVEDP rose from 12- to 29-mmHg and EF fell from 47% to 37%. During angina, there was a marked increase in the stiffness of the LV. The changes were reversible with resolution of angina. Barry et al, Circulation, 1974.

Presence of S4 with Aortic Stenosis (AS)

It has been noticed that atrial contraction was particularly intense in patients with obstruction to left ventricular outflow. Researchers wanted to determine whether the increased contraction in patients with AS is reflected in the presence of an S4, and conversely, whether the absence of an S4 could be correlated with the height of an A-wave and severity of obstruction of left atrial emptying. An S4 was recorded in thirty of forty-six AS patients. The S4 was 0.07 to 0.20 (mean 0.078-sec) from P onset. S4's were related to predominant A-waves. An S4 was recorded in all twenty-seven patients in which A-wave peak exceeded 13-mmHg and in only three who did not exceed 13-mmHg. S4 was recorded in all twenty-eight patients with LVEDP>=12-mmHg and two whose LVEDP was<12-mmHg. They found a relationship between the degree of obstruction, amount of LV thickening and elevation of LVEDP. The researchers conclude that the S4 is capable of separating patients with moderate or severe obstruction from those with mild obstruction.

The researchers continue to state that the S3 is divided into two components. Earlier, low frequency, inaudible vibrations are synchronous with and presumably result from left atrial contraction. The later, higher frequency, somewhat louder and audible vibrations occur the phase of ventricular filling resulting from atrial contraction and probably originate in the ventricle. Goldblatt et al, Circulation, 1962.

Murmurs

Summary: The presence of a variety of systolic murmurs is well understood. The goal of our efforts is to detect moderate and severe systolic murmurs, and all diastolic murmurs. No differentiation of cause of systolic murmurs would be done. The presence of systolic murmurs with AMI is also well documented and reasonably prevalent (a reported 17%). New systolic murmurs with AMI indicate poor prognosis and more severe infarction. Practical uses would be the following:

1. To diagnose AMI;
2. To detect patients with AMI and poor prognosis;
3. To monitor AMI patients for development of systolic murmurs;
4. To detect a common cause of systolic HF (valvular disease);
5. To detect hypertrophic obstructive cardiomyopathy.

Literature Summary: Systolic Murmur and AMI: There are three murmurs of significance associated with AMI. Mitral incompetence due to papillary muscle dysfunction (crescendo-decrescendo shape in the latter part of systole). Mitral incompetence due to papillary muscle rupture (decrescendo shape beginning after S1). Perforation of the ventricular septum (holosystolic murmur). Perloff et al, Progress in Cardiovascular Disease.

Sixteen hundred and fifty-three patients with AMI were studied. Of these, two hundred and eighty-three (17%) had a systolic murmur suggesting mitral incompetence. There was a higher incidence of systolic murmur in non-Q-wave AMI than in inferior or anterior Q-wave MI. Patients with systolic murmurs had higher hospital and one-year mortalities than those without systolic murmurs ($p<0.01$) and more likely to re-infarct 2.5-times earlier ($p<0.0001$). They examined univariate predictors of one-year mortality in non-Q-wave and Q-wave infarction. Of sixty-five variables tested, systolic murmur was ranked twelfth in non-Q-wave infarction (p=0.025), but fifty-first in Q-wave MI (p=0.671). Maisel et al, American Heart Journal.

New, soft systolic murmurs are frequently audible at the apex and may be caused by mitral regurgitation secondary to papillary dysfunction. A new, loud systolic murmur accompanied by a thrill suggest mitral regurgitation secondary to rupture of the head of the papillary muscle or a ventricular septal perforation. Pericardial friction rubs are heard in approximately 15% of AMI patients. Goldman and Braunwald, Primary Cardiology and Julian and Cowan, Cardiology.

Systolic Murmur and Aortic Stenosis: A group of forty-seven patients with aortic stenosis was studied. The patients were divided by severity of the stenosis into two groups. Two groups of normals (an unselected group of twenty, and a group of twenty subjects with innocent systolic ejection murmurs) were considered as well. Time from S1 and Q to peak of the murmur, ejection time, and maximal rate of rise of the carotid pulse were measured.

|  | Gradient < 50 mm | Gradient > 50 mm | Normal | P value | Comparison |
|---|---|---|---|---|---|
| S1-Peak of murmur | 0.195 +/− 0.036 | 0.197 +/− 0.036 | 0.134 +/− 0.010 | <0.01 | 1–3, 2–3 |
| Q-Peak of murmur | 0.247 +/− 0.029 | 0.250 +/− 0.035 | 0.187 +/− 0.015 | <0.01 | 1–3, 2–3 |

The measurement which correlated most highly with the degree of aortic stenosis was the timing of the peak of the systolic murmur. No normal individual with an innocent ejection murmur had a Q to peak time of longer than 0.24-sec. In the aortic stenosis group twenty-four patients had Q-peak times greater than 0.24-sec and twenty-two of these had severe stenosis. The authors concluded that a Q-peak time of greater than 0.24-sec strongly suggests severe aortic stenosis, whereas a short time less than 0.20-sec strongly denies such a diagnosis. Bonner et al, Circulation, 1973.

Pseudo-apexcardiogram

Summary: It was quite popular to record apexocardiograms twenty or so years ago and much was published in the literature. A-wave height was believed to be related to LV pressure and confirm the presence of a pathological S4. Practical uses of a pseudo-apexocardiogram would be:

1. To discriminate a pathological S4 from one more benign;
2. To confirm the presence of an S4;
3. To confirm elevated LV pressures and increased stiffness of the LV;
4. To diagnosis AMI and ischemia.

Current Status: An acoustic signal can be filtered in such a way as to approximate the apexocardiogram. One would expect that acoustic files with an S4 would display an A-wave similar to that in the literature.

Literature Summary: In some cardiac conditions, studies have shown a large A-wave in the apexcardiogram to be associated with an elevated left ventricular end diastolic pressure. "Further consideration, however, of the conditions which are marked by an atrial gallop or an exaggerated A-wave in the apexcardiogram suggests that the common denominator might be an altered pressure-volume relationship." During experiments with measurement of pressure volume loops, a closer relationship was maintained between A-wave height and distensibility of stiffness of the LV (change of pressure per unit change of volume) than the LVEDP itself. An S4 would occur when a small additional increment in volume resulting from atrial systole would lead to a brisk rise in pressure—when the ventricle was showing diminished distensibility. The author concludes that a large A-wave can be used to determine that a patient with chest pain is cardiac in origin. Craige in The Fourth Heart Sound.

Respiratory Sounds

Summary: This would be a useful parameter in differentiating cardiac from pulmonary causes in a patient with shortness of breath. Also, distinguishing between inspiration and expiration (e.g. by their relative durations) would enable one to distinguish between right and left sided sounds.

Short List of Measurements for Fingerprinting

| Measurement | Snapshot | | Monitoring | | Non-cardiac |
|---|---|---|---|---|---|
|  | CHF | ACS | CHF | ACS |  |
| P onset - S4 interval | Y | Y | Y | Y | N |
| Q onset - S1 interval | Y | ? | Y | Y | N |
| Q onset - S2 interval | Y | Y | Y | Y | N |
| S1 or S2 energy content | ? | Y | Y | Y | N |
| S1/S2 ratio | ? | Y | Y | Y | N |
| Change in heart sounds during ischemia | Maybe | Y | Maybe | Y | N |
| Murmurs | Y | Y | Y | Y | N |
| Pseudo-Apexocardiogram | Y | Y | Y | Y | N |
| Respiratory Sounds | Y | N | Y | N | Y |

| Measurement | Theory | Clinical Use |
| --- | --- | --- |
| P onset - S4 interval | The closer the S4 to p wave onset:<br>1. the higher LVEDP is<br>2. the more likely the S4 is "pathological"<br>3. the more likely a patient with AMI has bad prognosis | 1. Any application where LV pressure and its change is important.<br>2. To improve diagnosis of AMI and ischemia<br>3. To determine severity and/or prognosis of AMI |
| Q onset - S1 interval | Electromechanical delay believed to be related to myocardial contractility and abnormal electrical conduction. | 1. To improve diagnosis of HF (by longer QS1)<br>2. To evaluate change in myocardial contractility or HF condition<br>3. To confirm Mortara calls of LBBB or v-pacing |
| Q onset - S2 interval | Electromechanical systole approximately equal to isovolumic contraction plus ejection time. Shown to be shortened by AMI and longer in HF than in normals. Believed to lengthen during recovery of AMI if good prognosis. | 1. Assist in diagnosis of AMI and ischemia (by shortening)<br>2. Prognosis of AMI<br>3. Assist in diagnosis of HF (by lengthening)<br>4. Evaluate change in HF or ischemic condition, or recovery from AMI |
| S1 or S2 energy content | S1 intensity is believed to relate to max dP/dt or ventricular contractility, while S2 intensity to isovolumic relaxation (diminished S2 = impaired relaxation). | 1. Diagnosis of AMI<br>2. Prognosis of AMI patients<br>3. Monitoring for change in LV function |
| S1/S2 ratio | Intensity of S1 and S2 by auscultation has been shown to change with AMI, in particular. S2's that diminish with AMI have been shown to increase during recovery from AMI | 1. Diagnosis of AMI<br>2. Prognosis of AMI patients<br>3. Monitoring for change in LV function |
| Change in heart sounds and ECG during ischemia | Hemodynamic/mechanical changes occur in the heart before ECG changes and symptoms occur during an ischemic event | 1. Heart sounds should improve detection of ischemia<br>2. Earlier detection of ischemia with sound than by ECG alone<br>3. For monitoring, time course of ischemic event |
| Murmurs | Acoustic vibrations due to valvular disease and stenosis are well known and accepted. | There are 3 potential product uses:<br>1. Simply to state systolic or diastolic murmur detected.<br>2. Along with ECG to diagnose specific conditions such as HOCM<br>3. To indicate increased severity of AMI with systolic murmur |
| Pseudo-Apexocardiogram | A true apexocardiogram converts cardiac tissue movement into a waveform that has been used to evaluate cardiac function, in particular, atrial contraction by the a-wave. The greater the amplitude of the a-wave (the more palpable the atrial contraction), the more likely there is cardiac pathology. | 1. To differentiate pathological S4's from those more benign<br>2. To confirm the presence of S4<br>3. To confirm elevated LV pressures and increased stiffness<br>4. To diagnose AMI and ischemia |
| Respiratory Sounds | Physicians routinely listen for lung sounds on patients short of breath. | 1. To differentiate cardiac from pulmonary causes in a patient short of breath |

| Measurement | ACS | CHF |
| --- | --- | --- |
| P onset - S4 interval | The closer the S4 to p wave onset:<br>1. the higher LVEDP is<br>2. the more likely the S4 is "pathological" and can be used to confirm diagnosis of ischemia or AMI<br>3. the more likely a patient with AMI has bad prognosis | 1. To monitor change in LV pressure with treatment, especially if there is ischemia with HF |

| Measurement | ACS | CHF |
|---|---|---|
| | 4. the younger an MI is (i.e., used for aging of infarcts) | |
| Q onset -S1 interval | 1. To evaluate change in myocardial contractility with acute events. | 1. To improve diagnosis of HF (by longer QS1) 2. To evaluate change in myocardial contractility or HF condition |
| Q onset - S2 interval | 1. Assist in diagnosis of AMI and ischemia (by shortening) 2. Prognosis of AMI 3. Evaluate change in ischemic condition, or recovery from AMI | 1. Assist in diagnosis of HF (by lengthening) 2. Evaluate change in HF |
| S1 or S2 energy content | 1. Diagnosis of AMI 2. Prognosis of AMI patients 3. Monitoring for change in LV function | 1. Monitoring for change in LV function |
| S1/S2 ratio | 1. Diagnosis of AMI 2. Prognosis of AMI patients 3. Monitoring for change in LV function | 1. Monitoring for change in LV function |
| Change in heart sounds and ECG during ischemia | 1. Heart sounds should improve detection of ischemia 2. Earlier detection of ischemia with sound than by ECG alone 3. For monitoring, time course of ischemic event | |
| Murmurs | 1. Simply to state systolic or diastolic murmur detected. 2. To diagnose AMI 3. To indicate increased severity of AMI with systolic murmur | 1. To state systolic or diastolic murmur detected. |
| Pseudo-Apexocardiogram | 1. To differentiate pathological S4's from those more benign 2. To confirm the presence of S4 3. To confirm elevated LV pressures and increased stiffness 4. To diagnose AMI and ischemia | 1. To differentiate pathological S4's from those more benign 2. To confirm the presence of S4 3. To confirm elevated LV pressures and increased stiffness |
| Respiratory Sounds | | 1. To differentiate cardiac from pulmonary causes in a patient short of breath |

Using Heart Sound Information and ECG to Assess Left Ventricular Function

People with heart disease often develop poor left ventricular function. This can result in poor quality of life and high mortality. The cardiac cycle is divided into systole (when the heart is actively contracting) and diastole (when the heart is relaxing and filling for the next contraction). An individual can have systolic dysfunction, diastolic dysfunction or both.

Attempts have been made in the past to non-invasively assess left ventricular function. Weissler et al, Systolic time intervals in heart failure in man, 1968, Circulation, 37: 149–159. Others have studied the concept of systolic time intervals using a combination of phonocardiology and apexcardiograms. These researchers studied the timing of various components of systole (pre-ejection time, ejection period, etc) to assist in diagnosis and prognosis of cardiac conditions.

Figure 6:
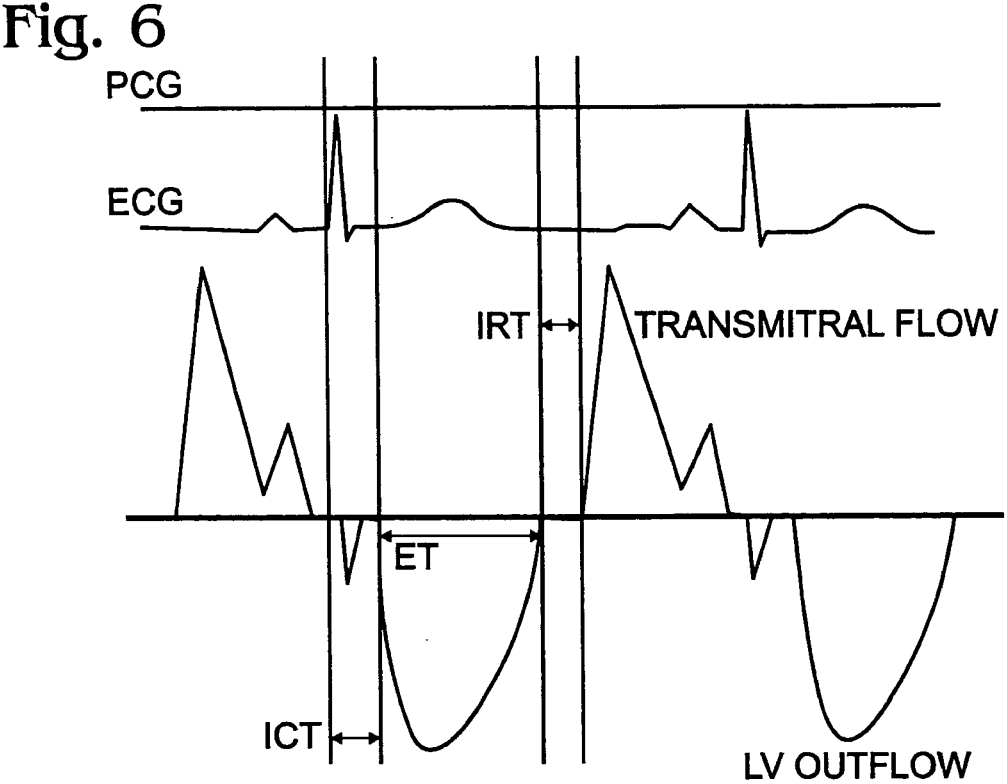
FIGS. 6 and 7 are related waveform-like illustrations useful in demonstrating one use of the present invention.
Figure 7:
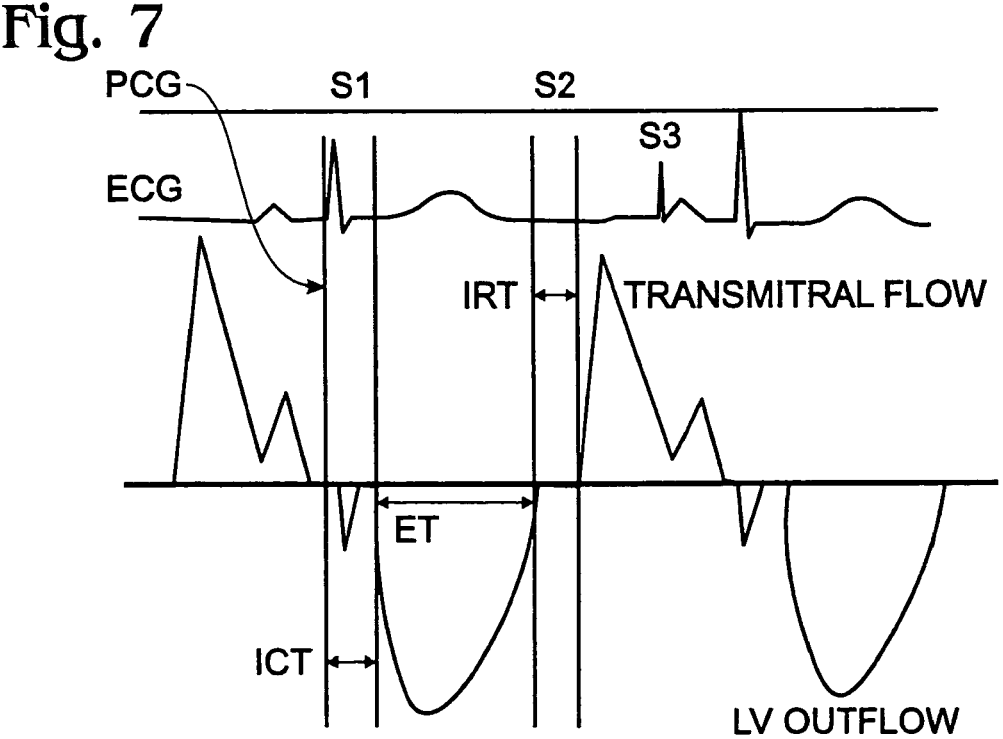
Figure 9:
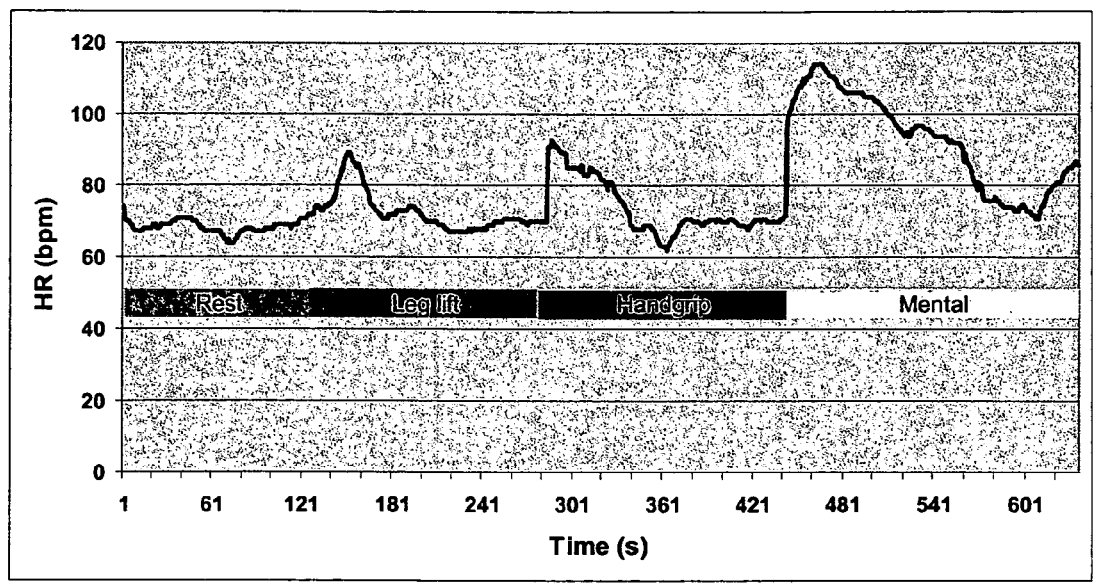
FIGS. 9–32, inclusive, present graphical illustrations of "fingerprinting" performed by practice of the present invention with respect to a first subject, Subject A. These illustrations show time-based values of several different categories of fingerprints under four different non-stress and stress conditions invoked for the Subject.
Figure 10:
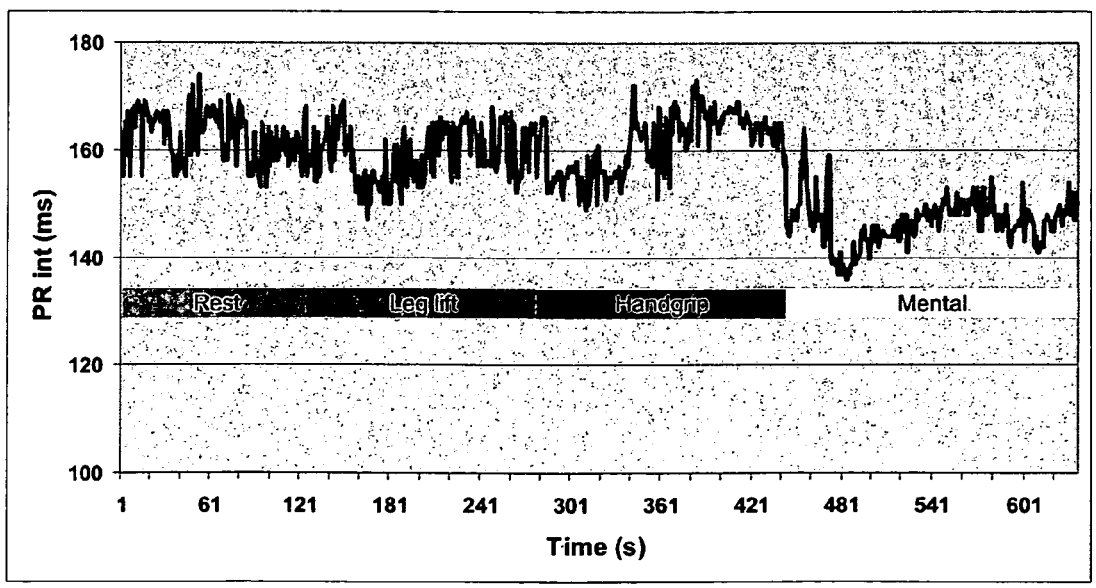
Figure 11:
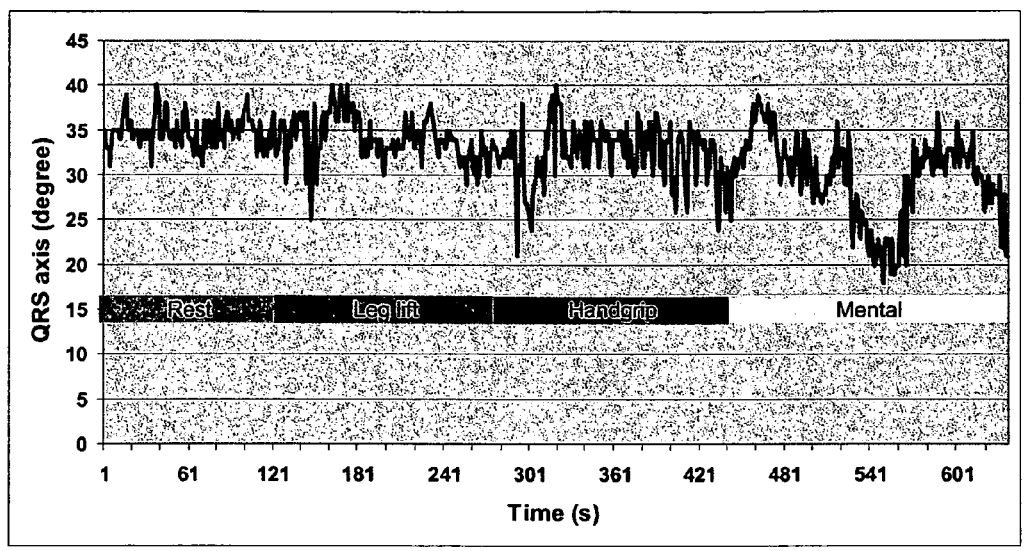
Figure 12:
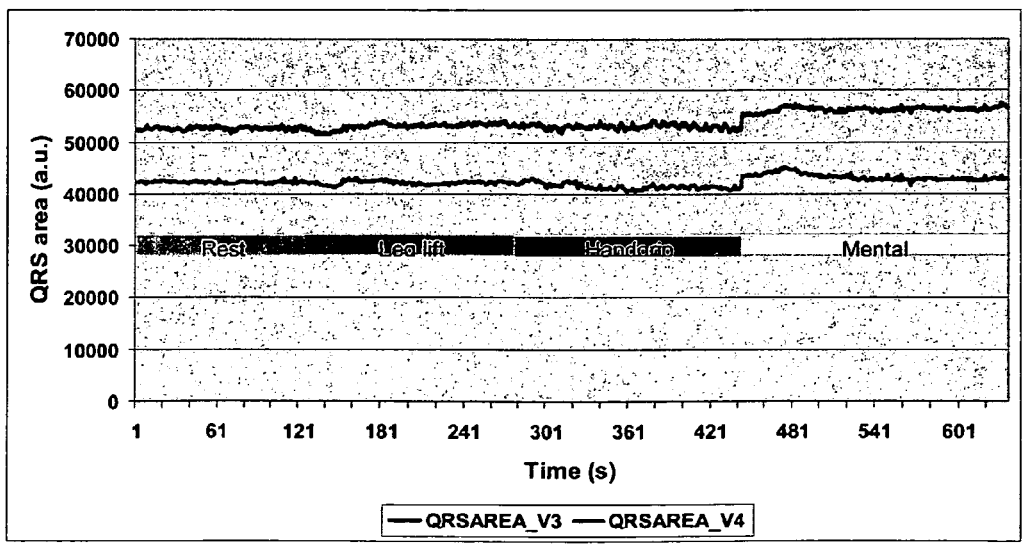
Figure 13:
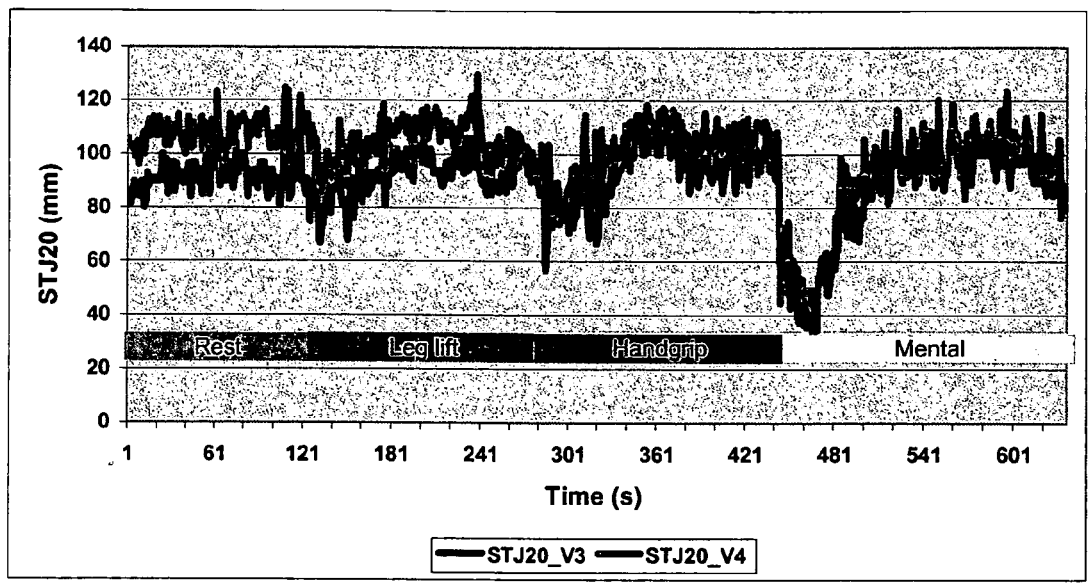
Figure 14:
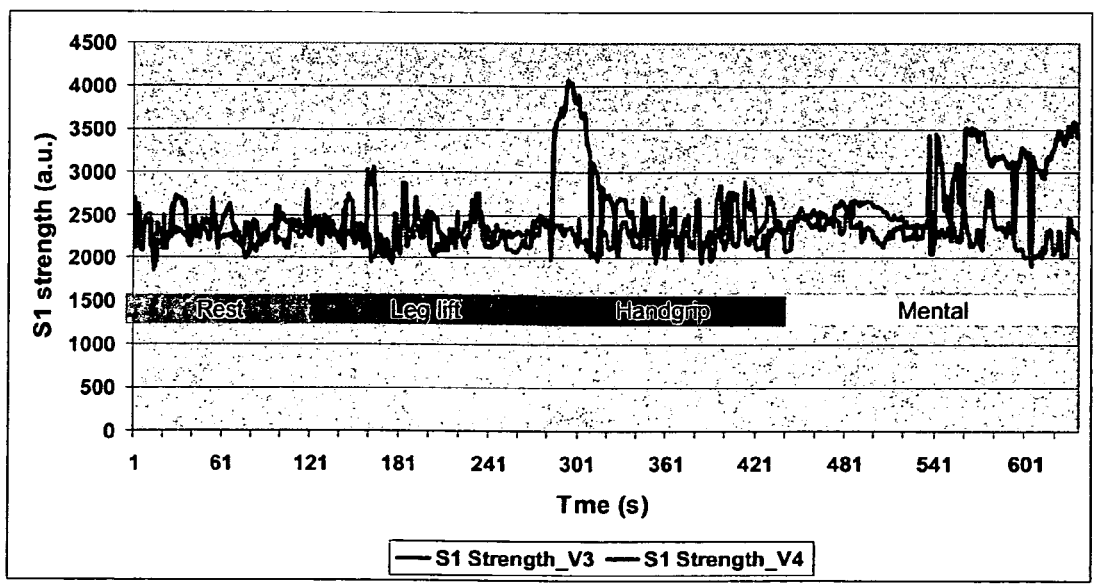
Figure 15:
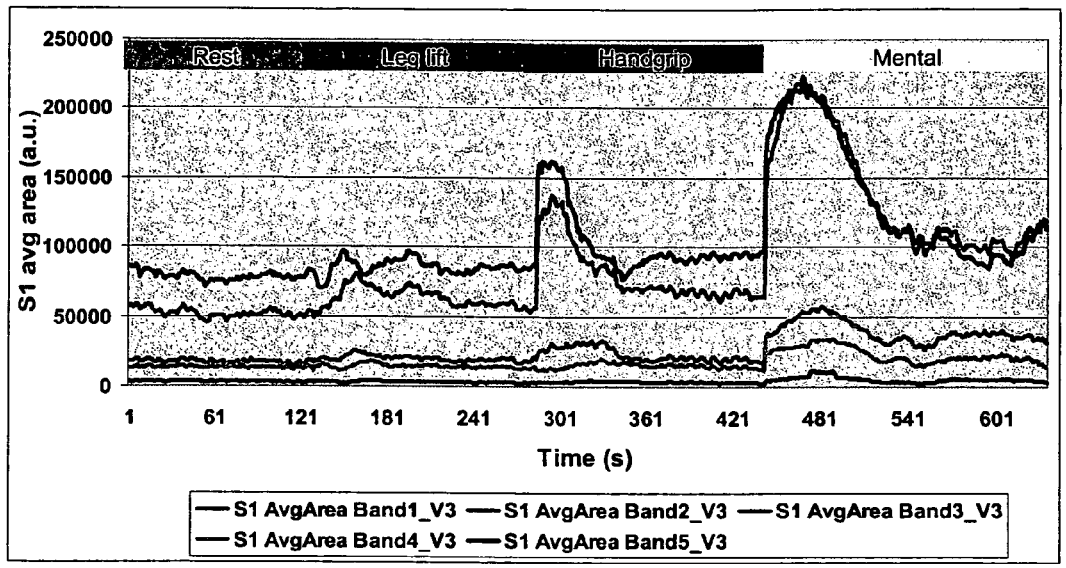
Figure 16:
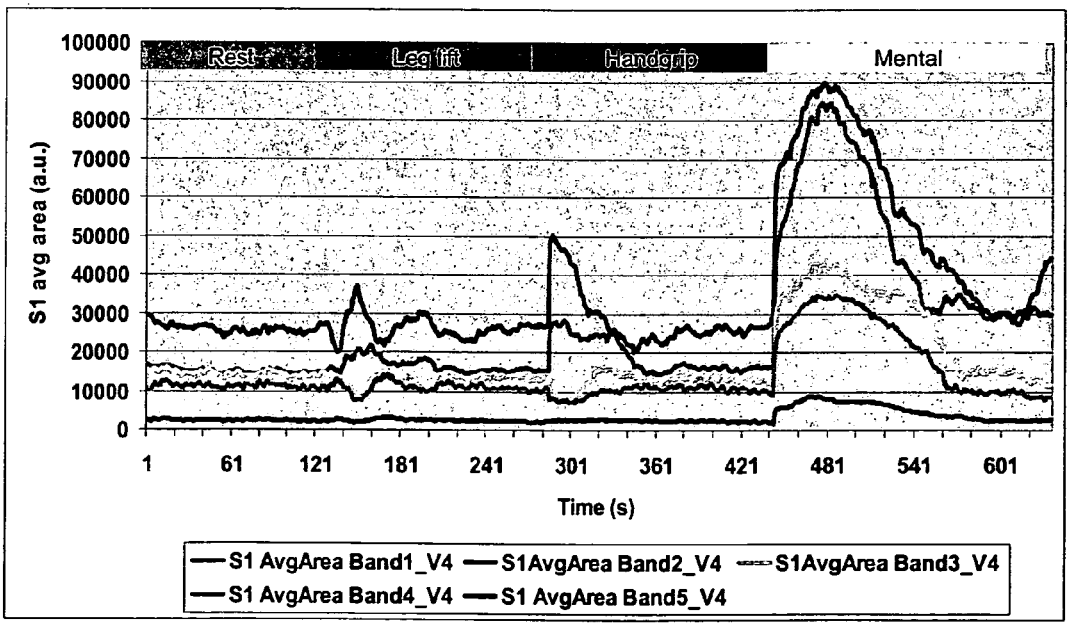
Figure 17:
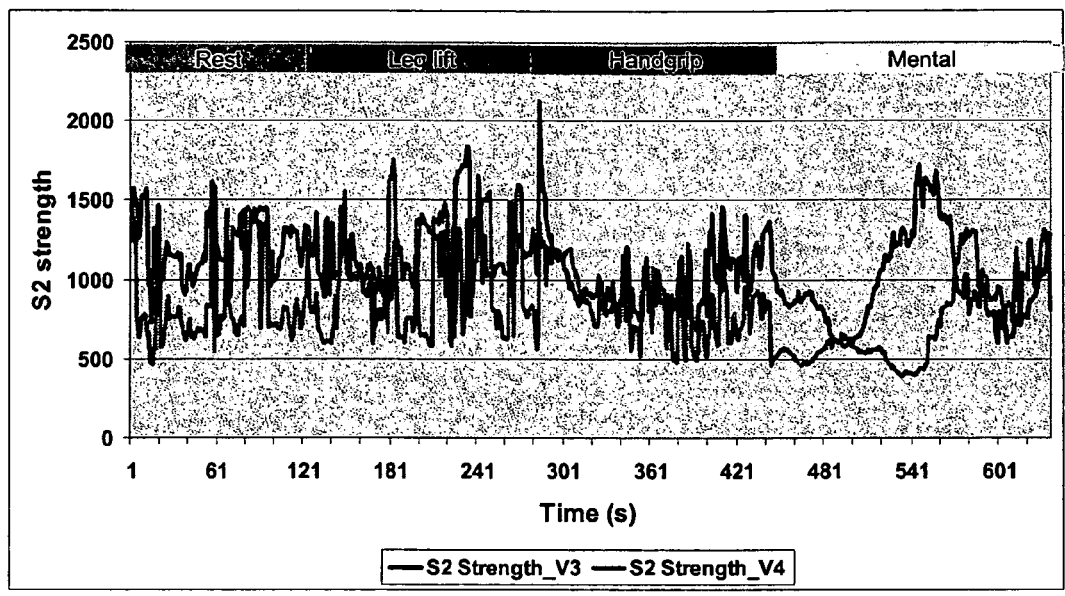
Figure 18:
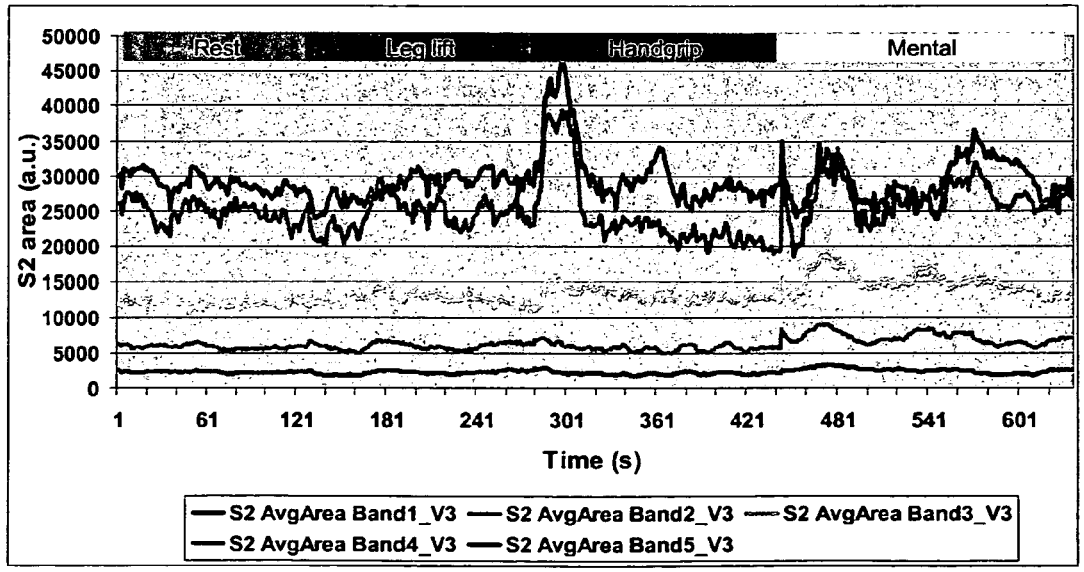
Figure 19:
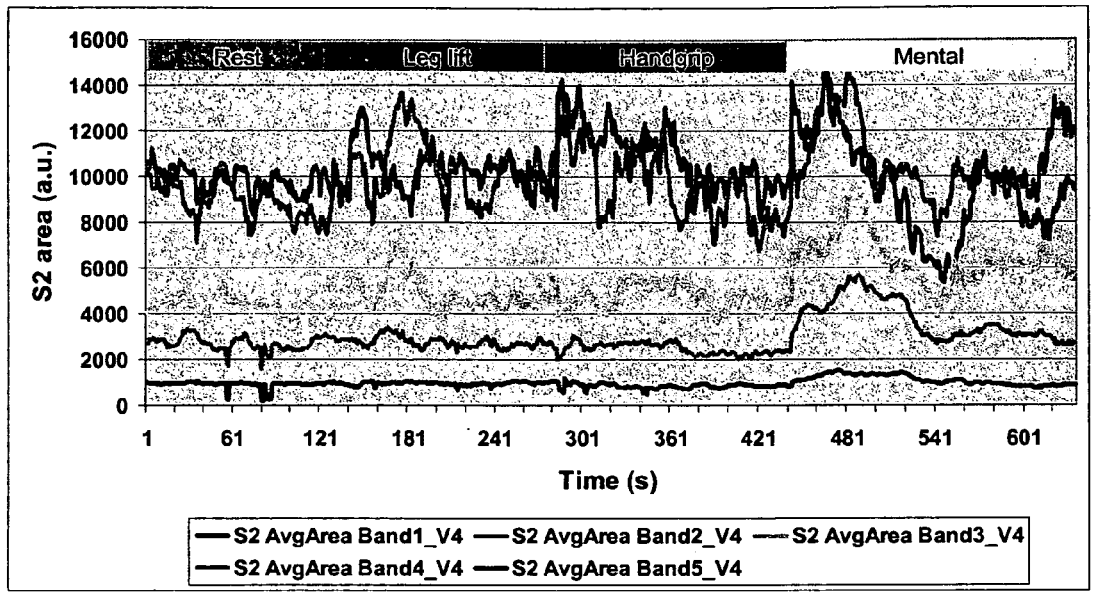
Figure 20:
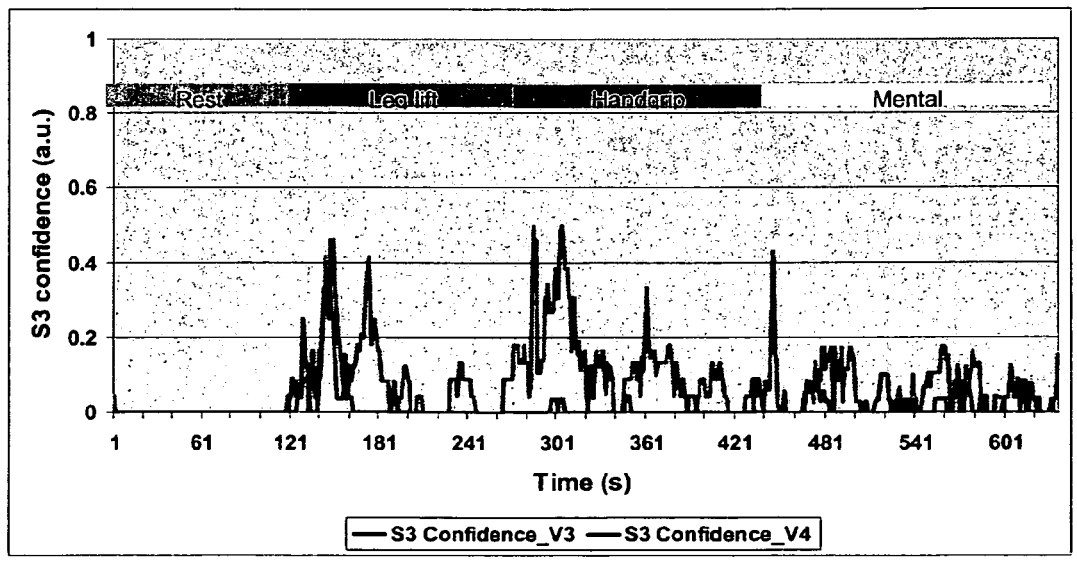
Figure 21:
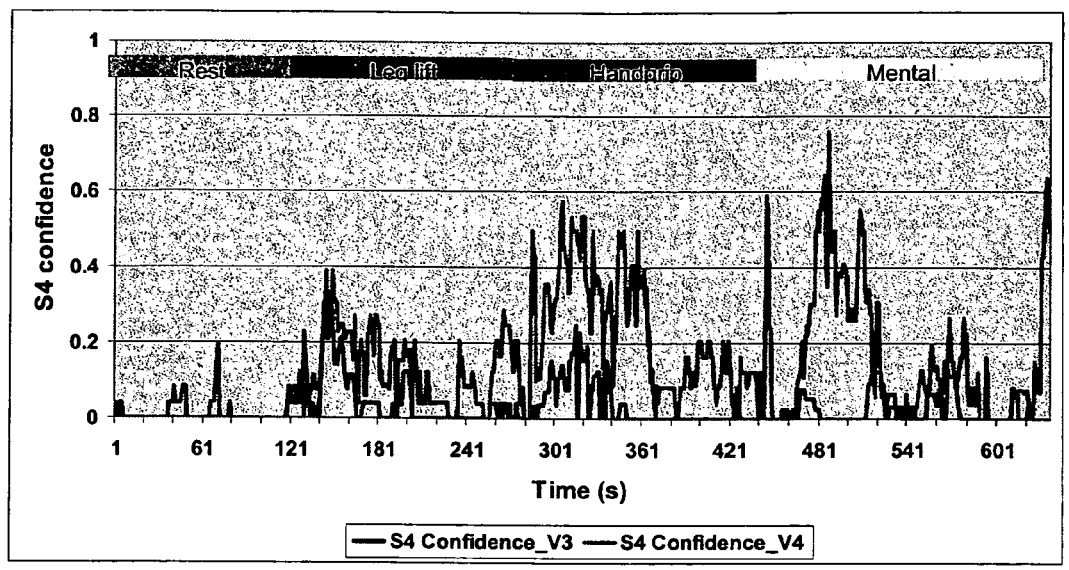
Figure 22:
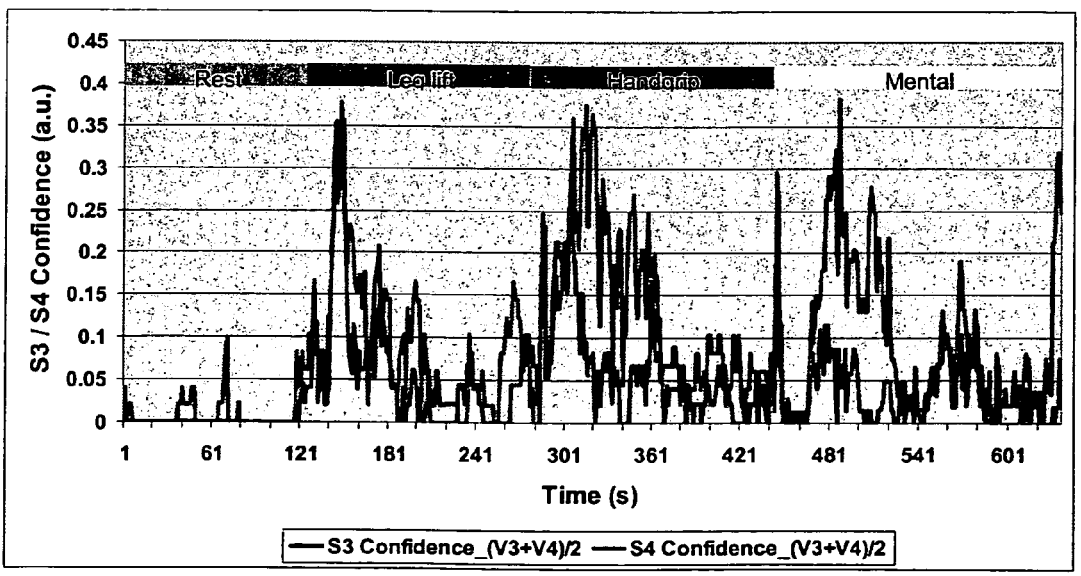
Figure 23:
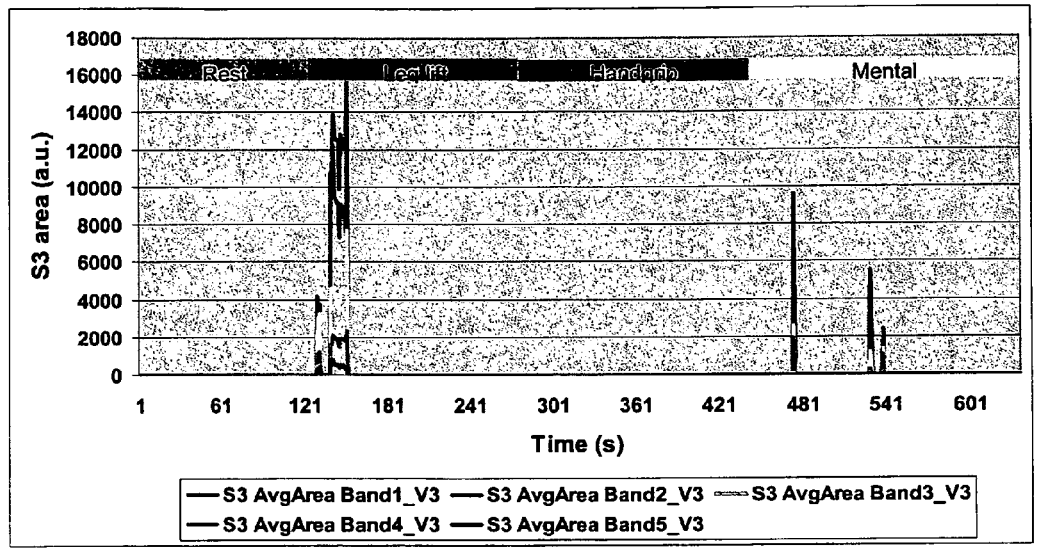
Figure 24:
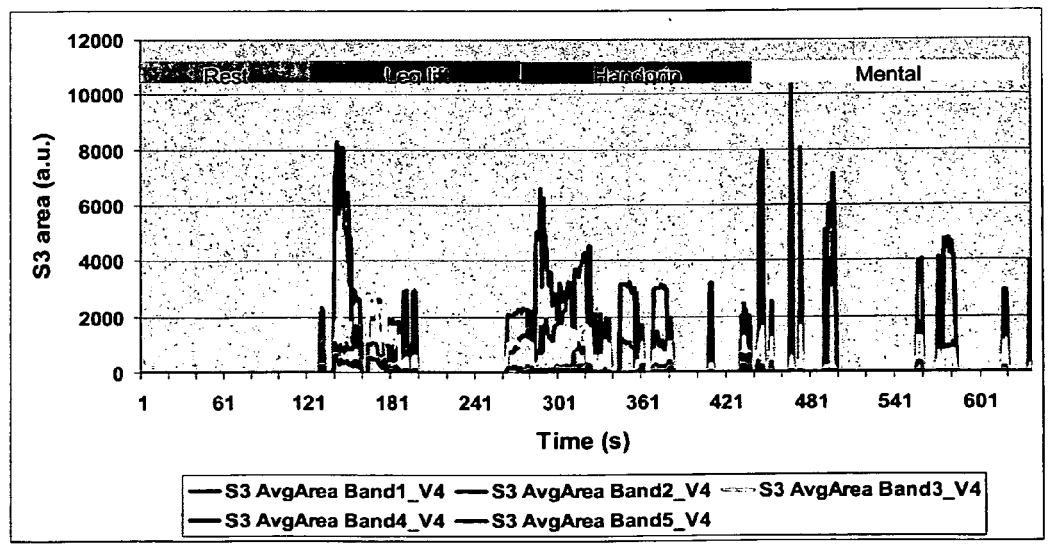
Figure 25:
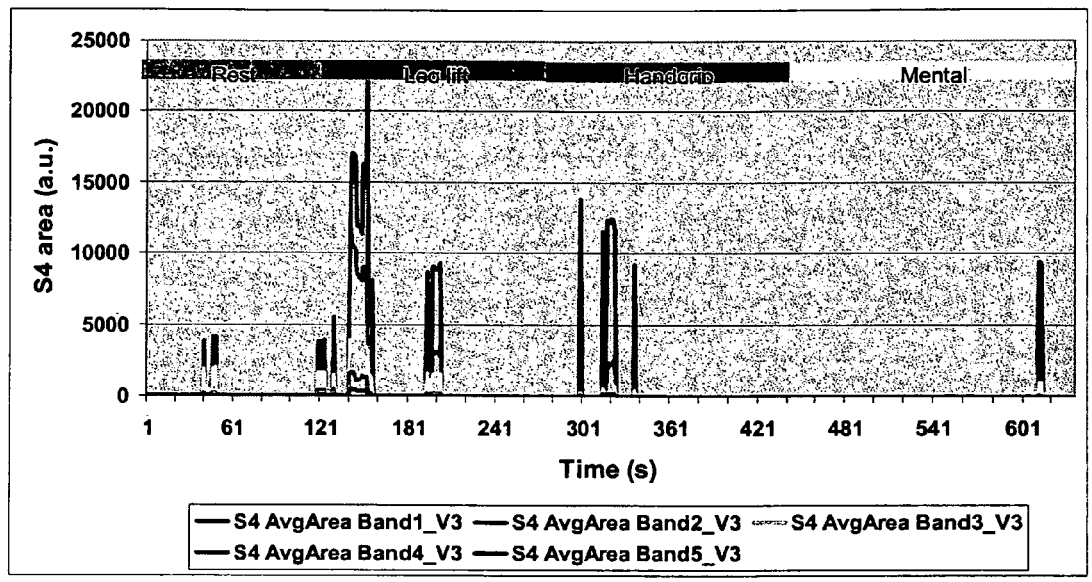
Figure 26:
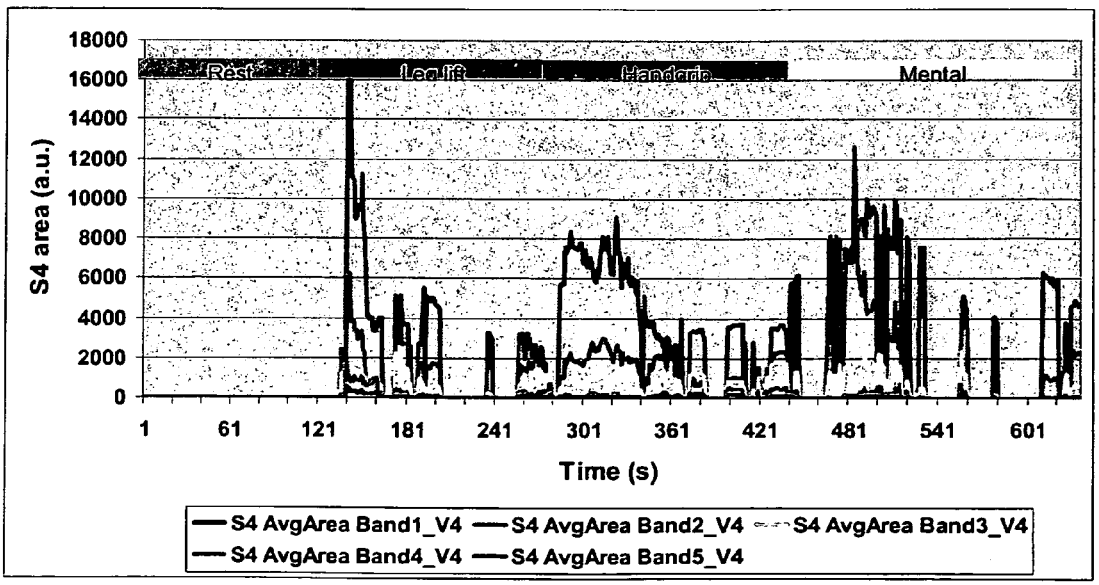
Figure 27:
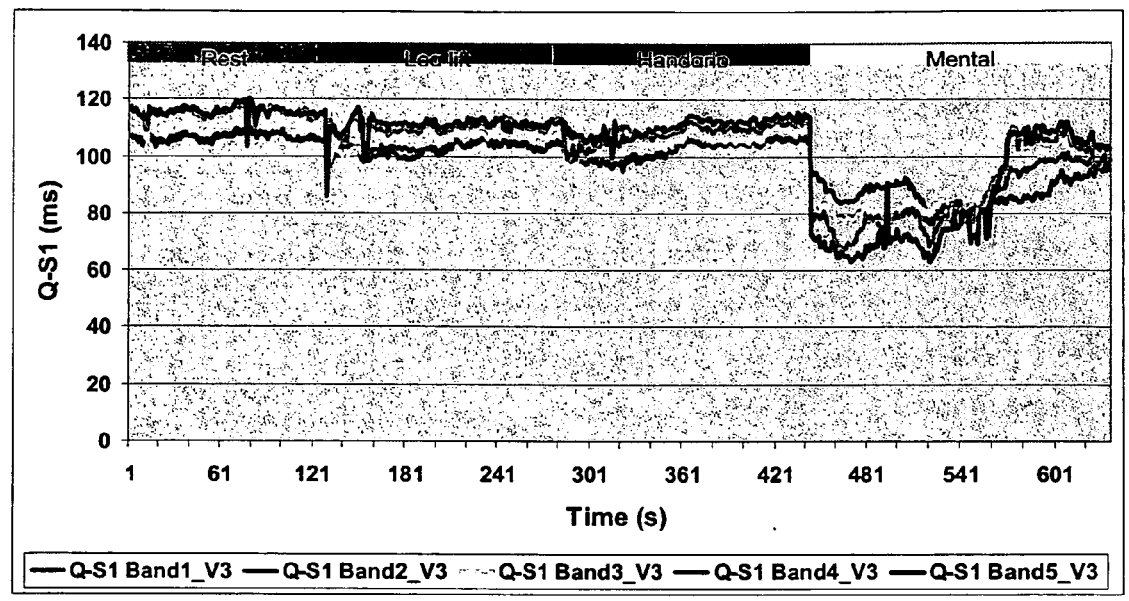
Figure 28:
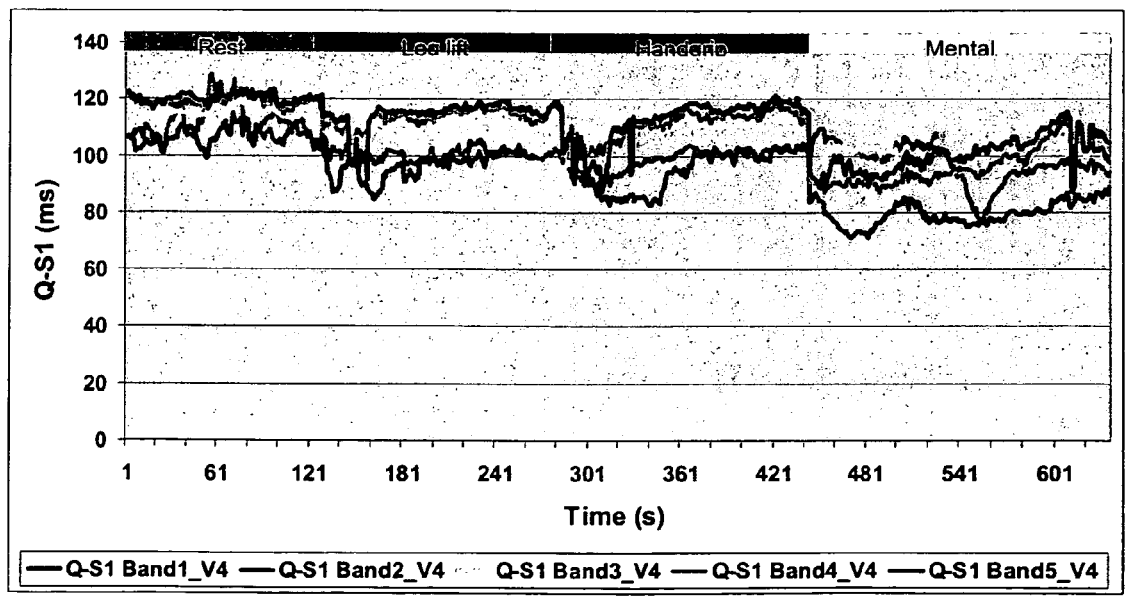
Figure 29:
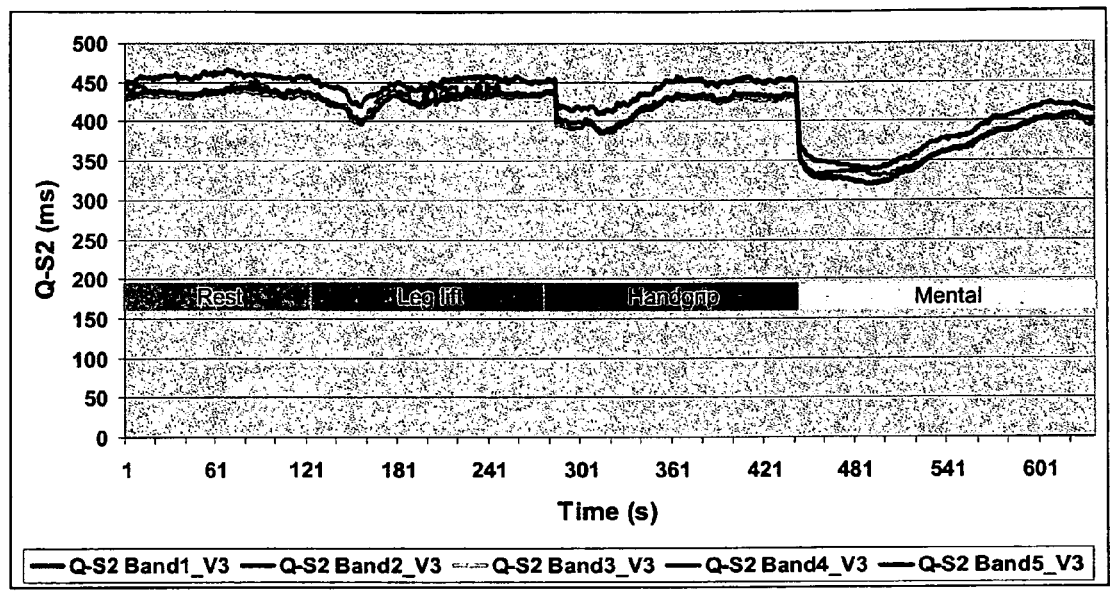
Figure 30:
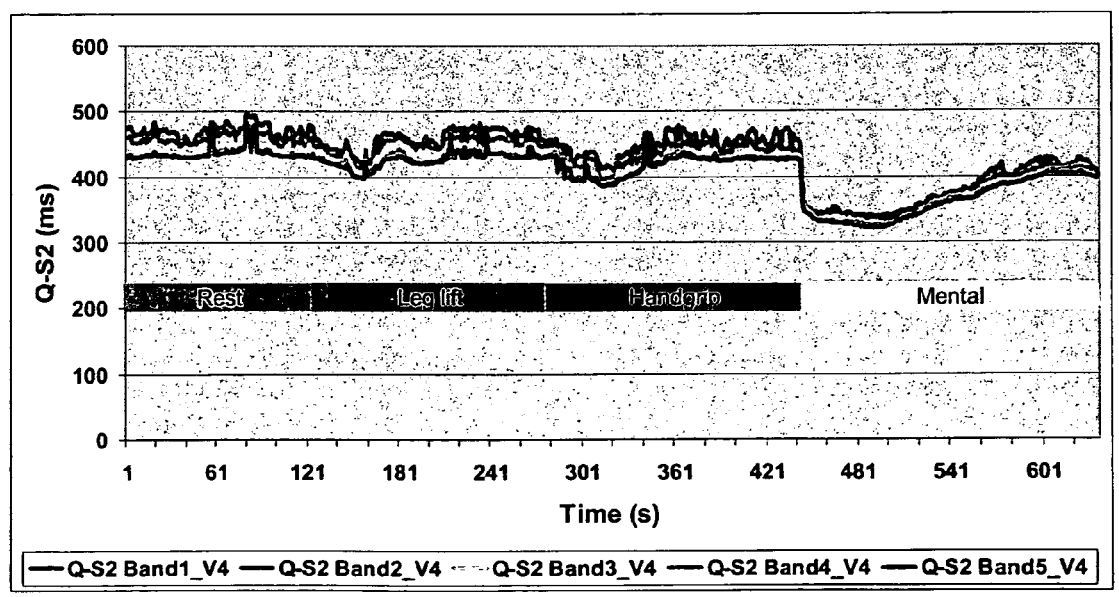
Figure 31:
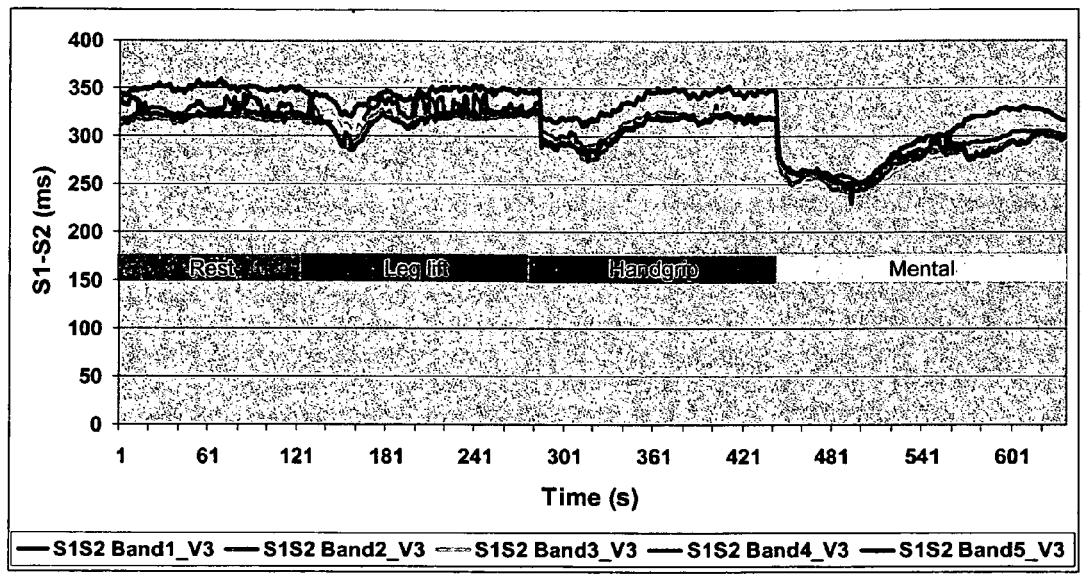
Figure 32:
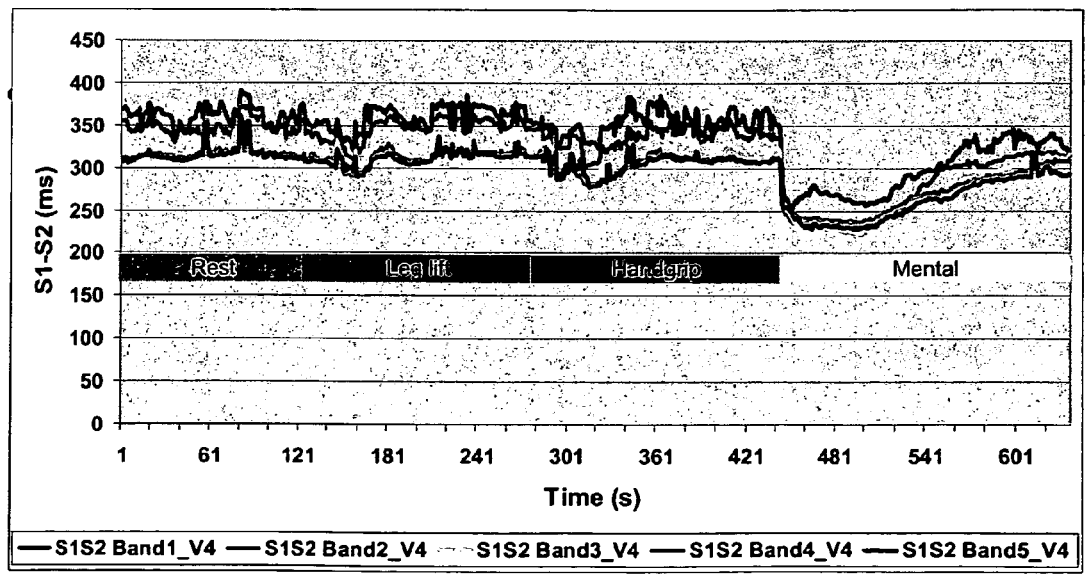
Figure 33:
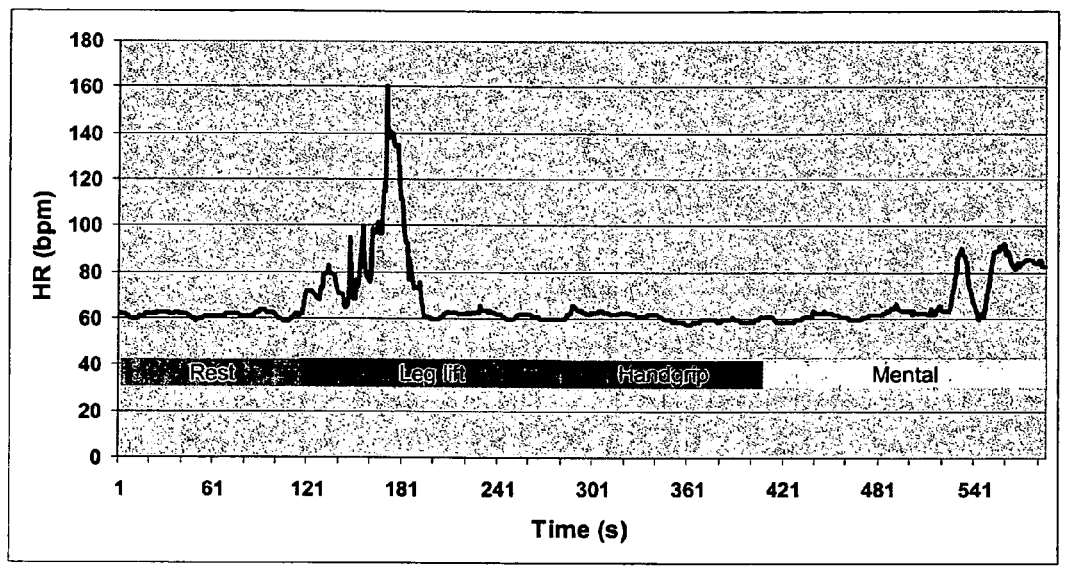
FIGS. 33–56, inclusive, present, for a different, second subject, Subject B, graphical fingerprint illustrations similar to those seen in FIGS. 9–32, inclusive.
Figure 34:
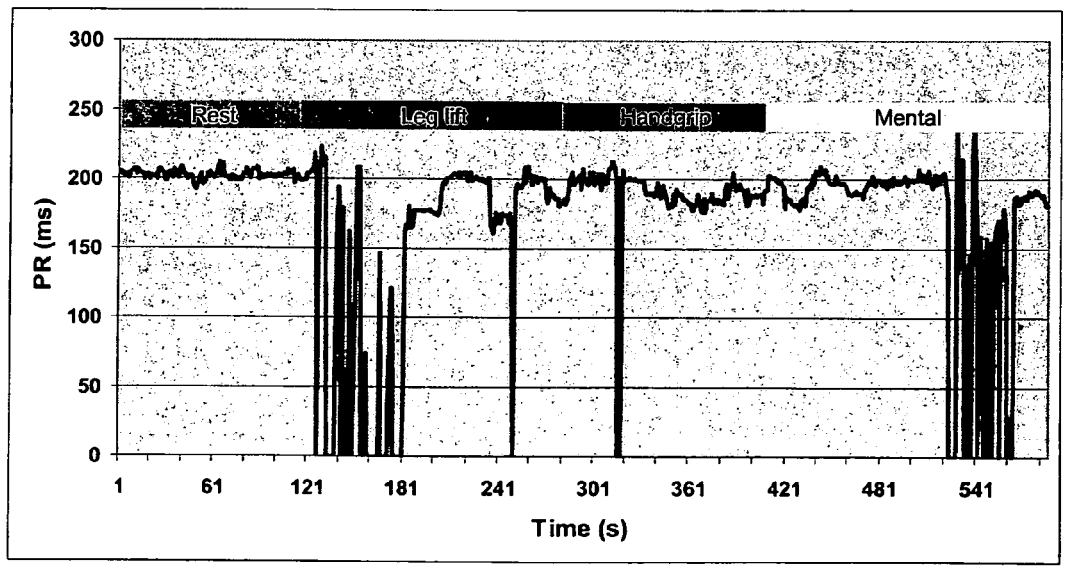
Figure 35:
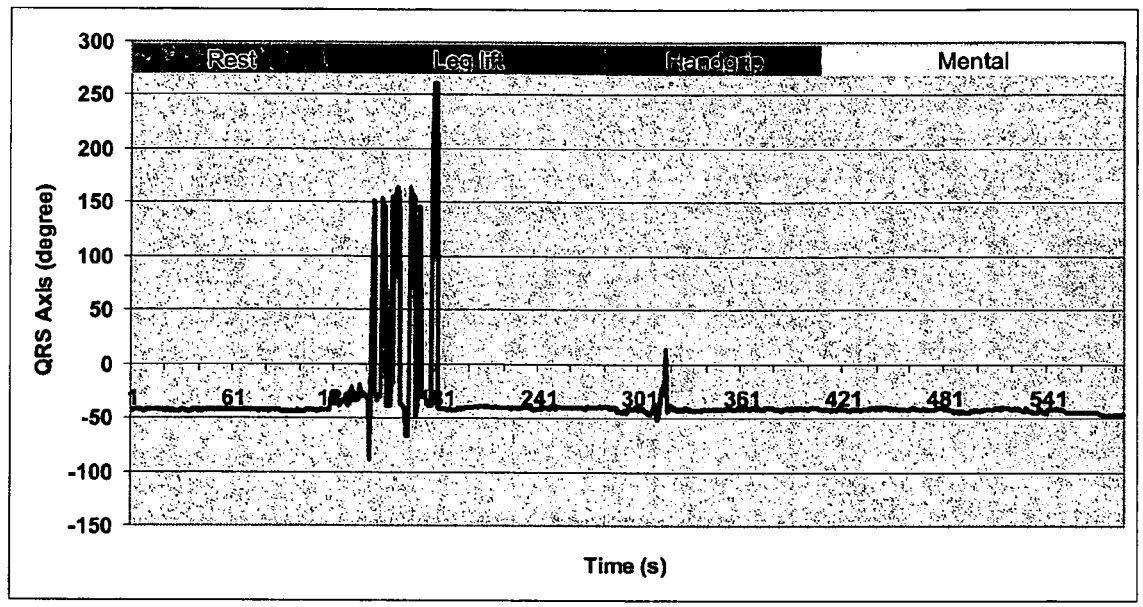
Figure 36:
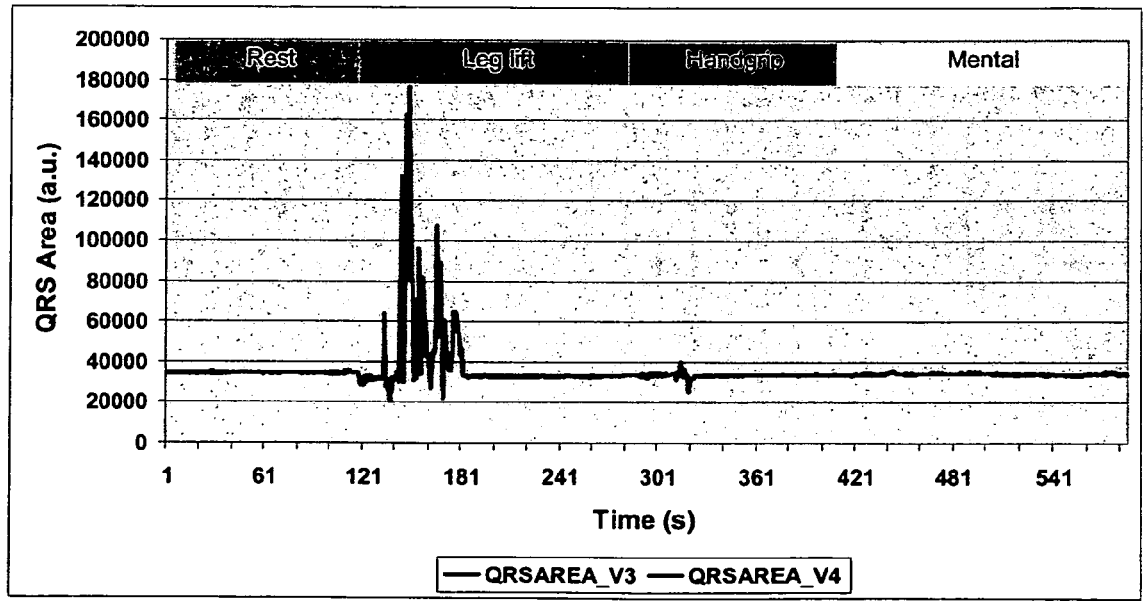
Figure 37:
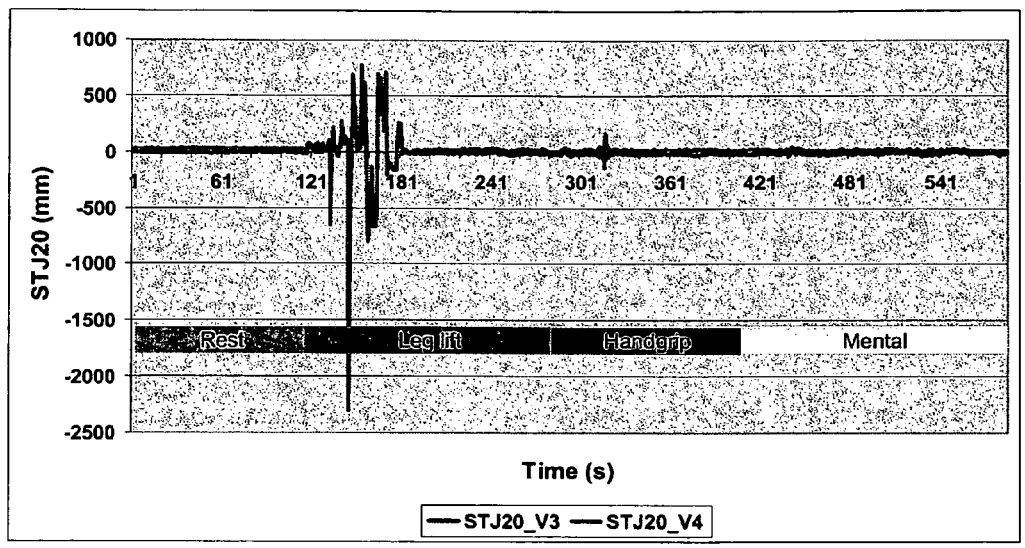
Figure 38:
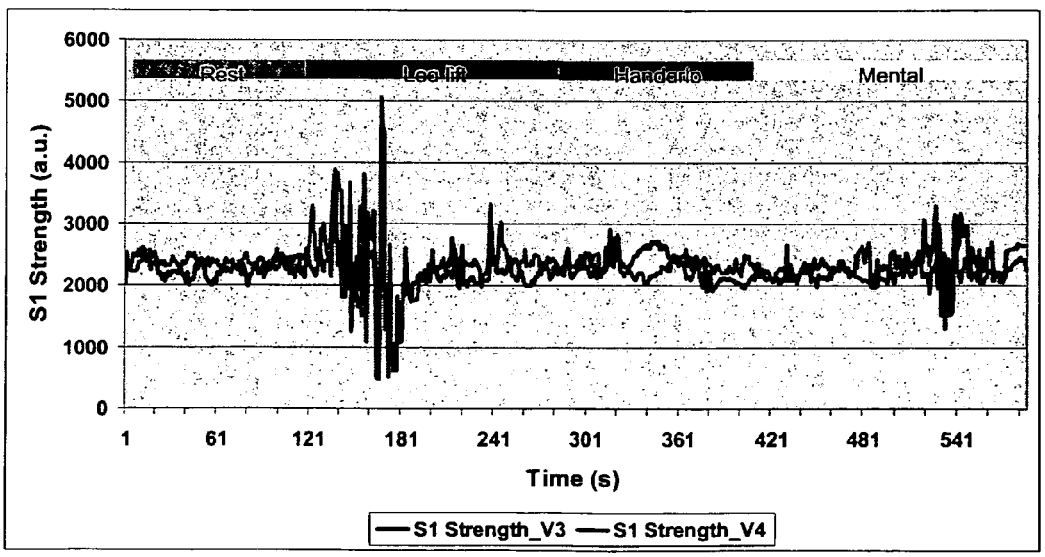
Figure 39:
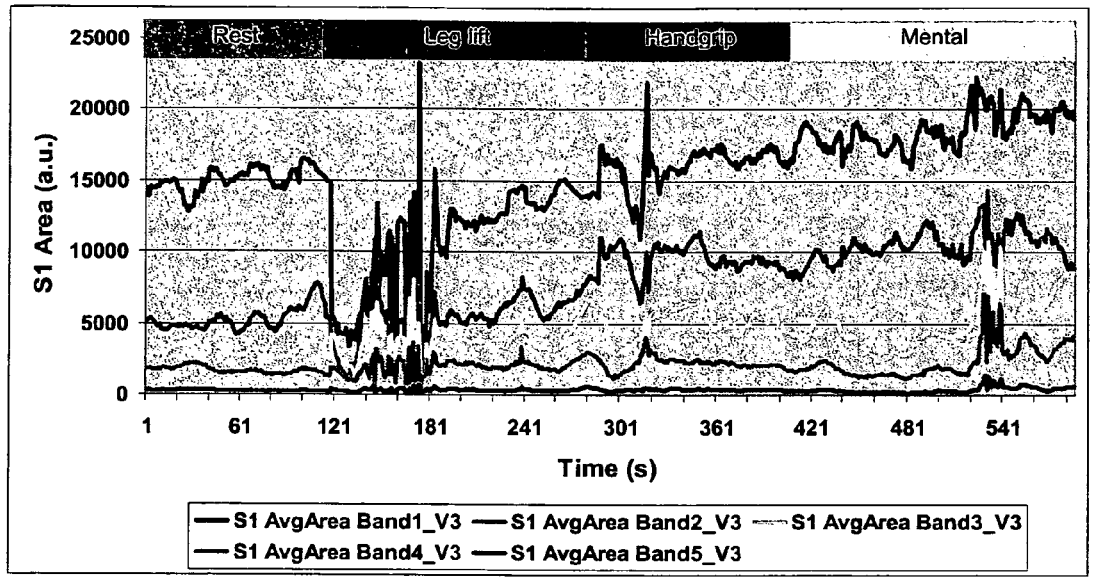
Figure 40:
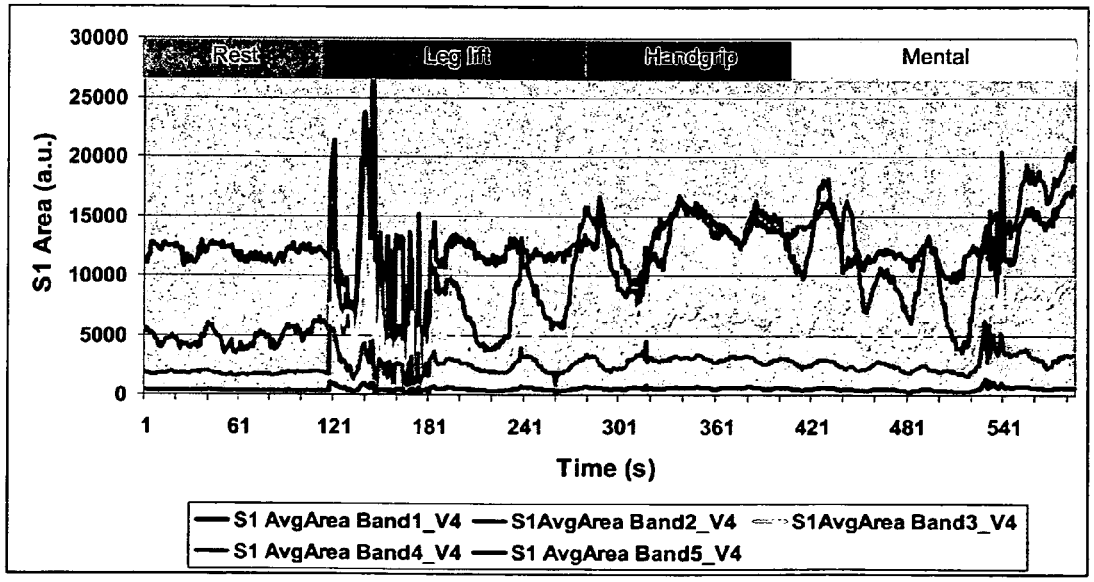
Figure 41:
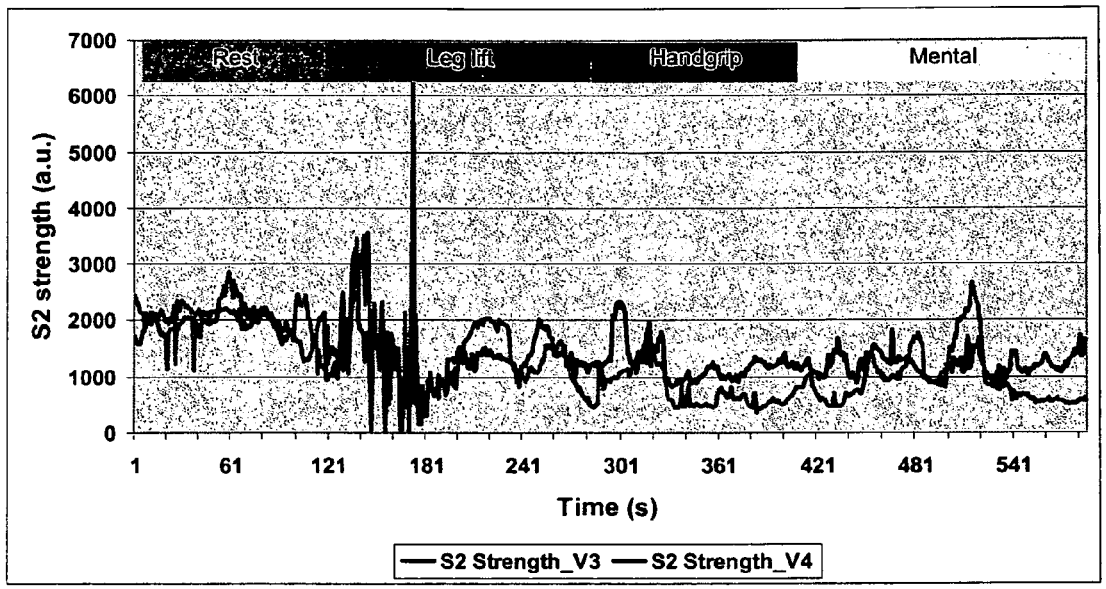
Figure 42:
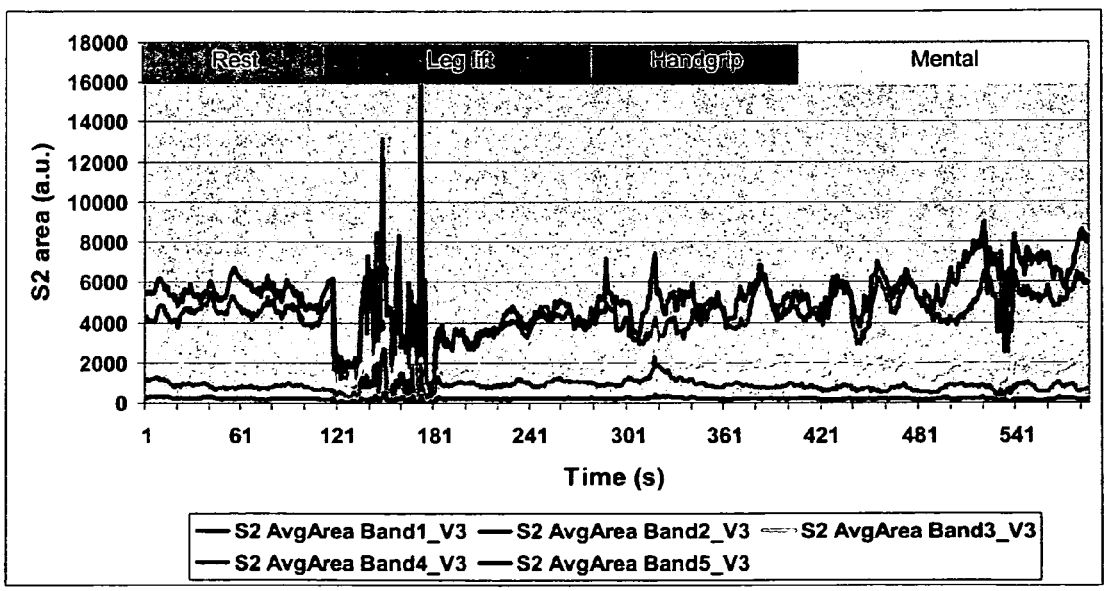
Figure 43:
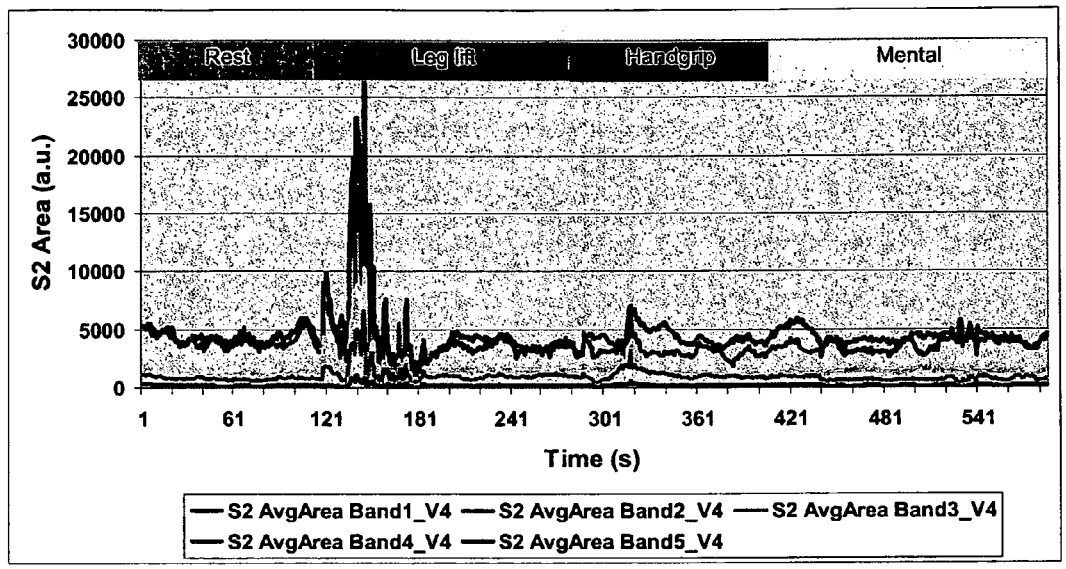
Figure 44:
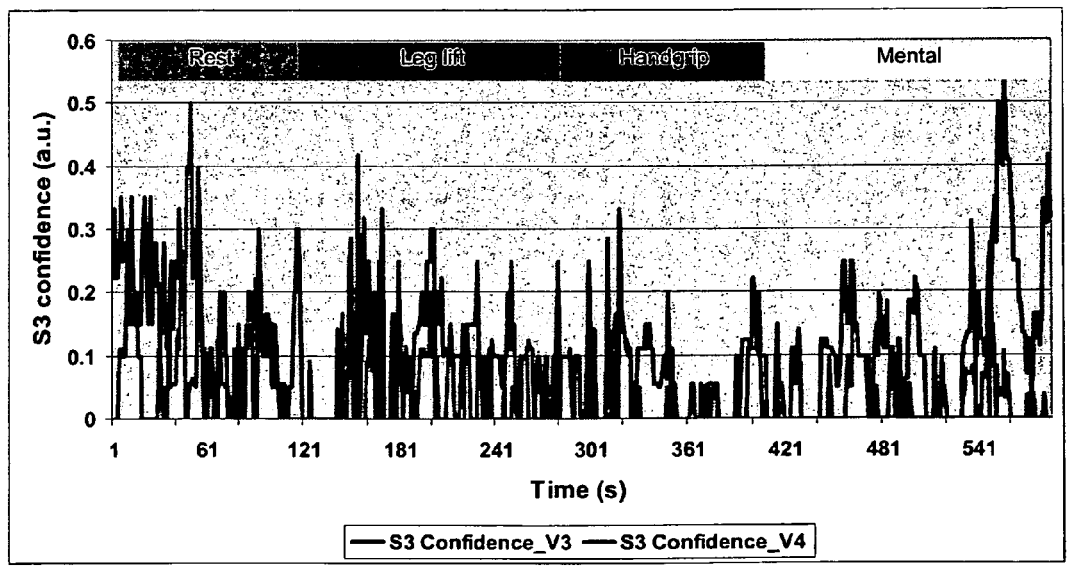
Figure 45:
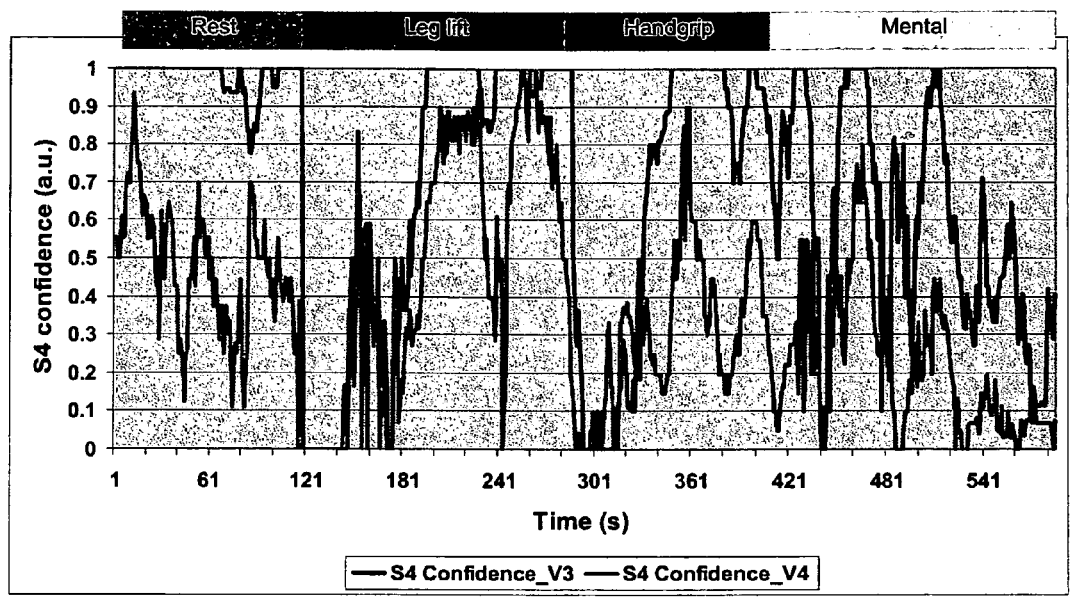
Figure 46:
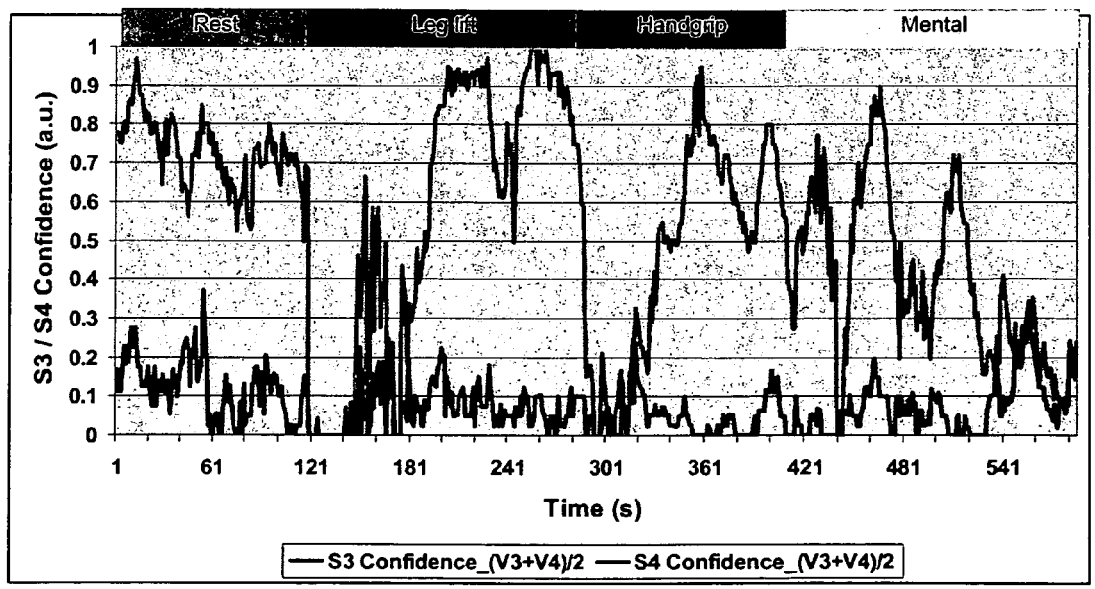
Figure 47:
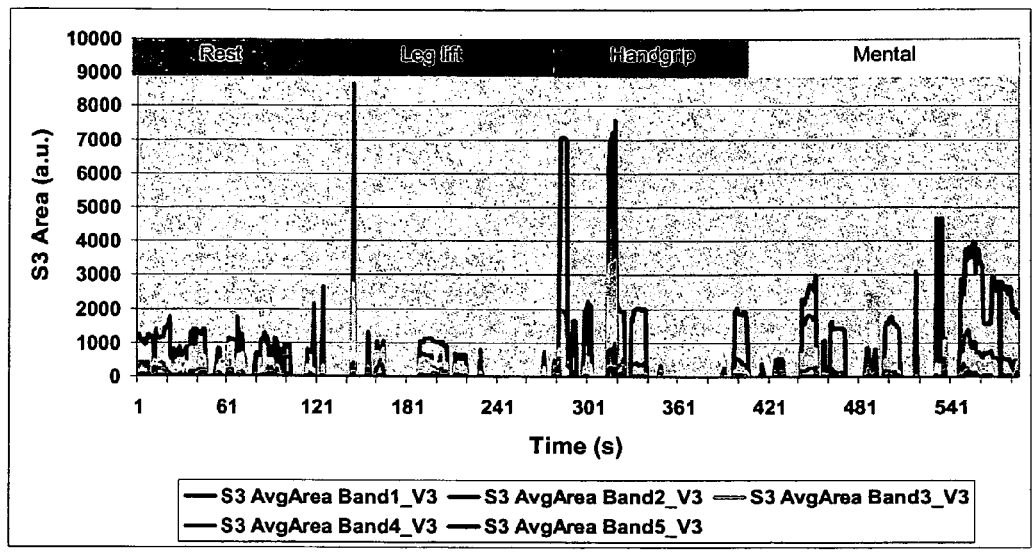
Figure 48:
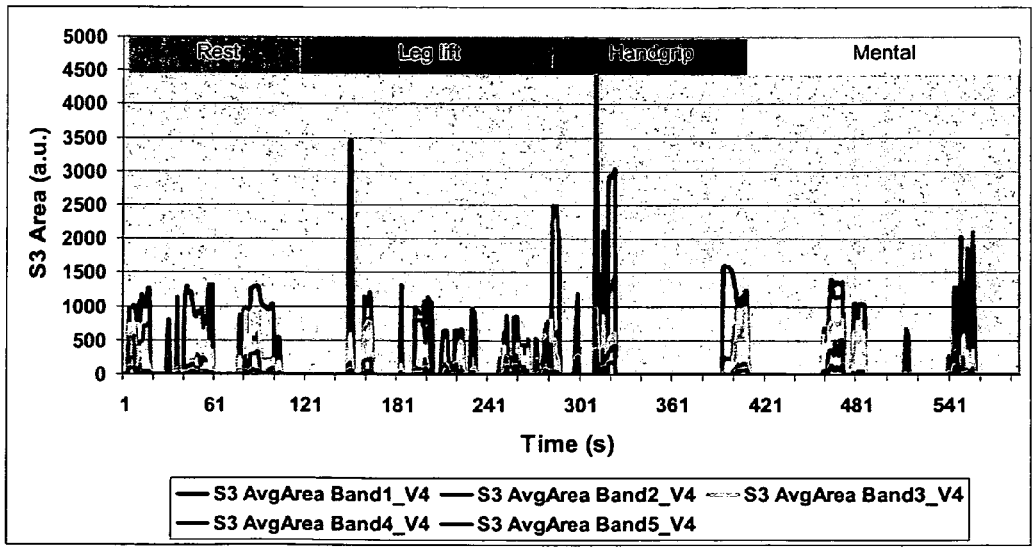
Figure 49:
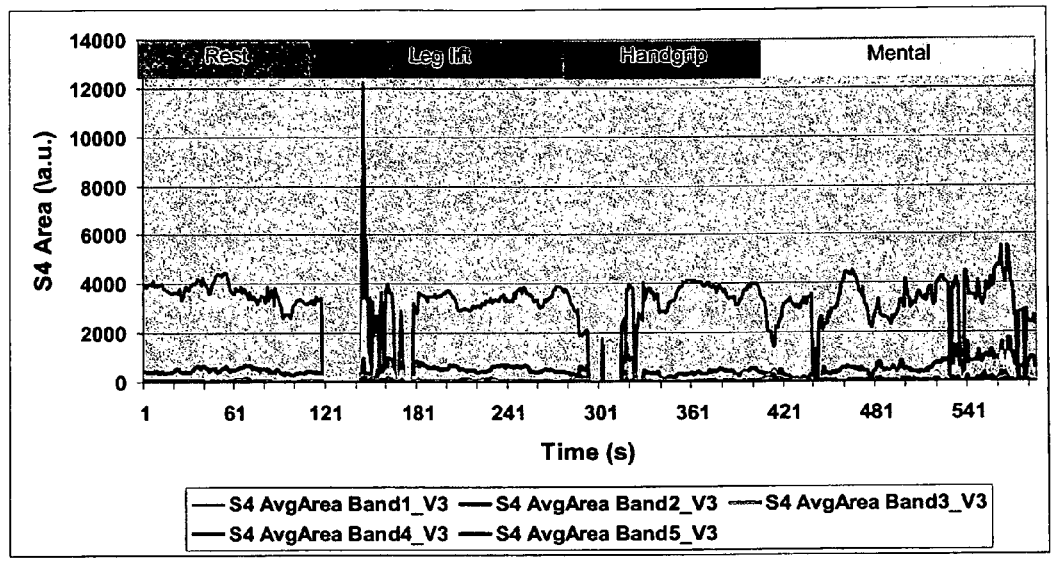
Figure 50:
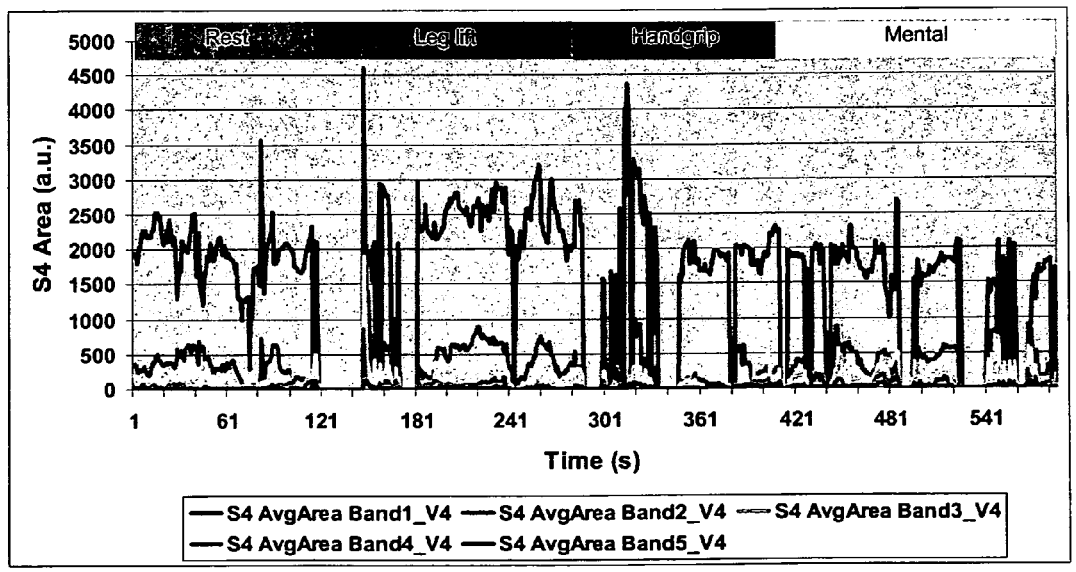
Figure 51:
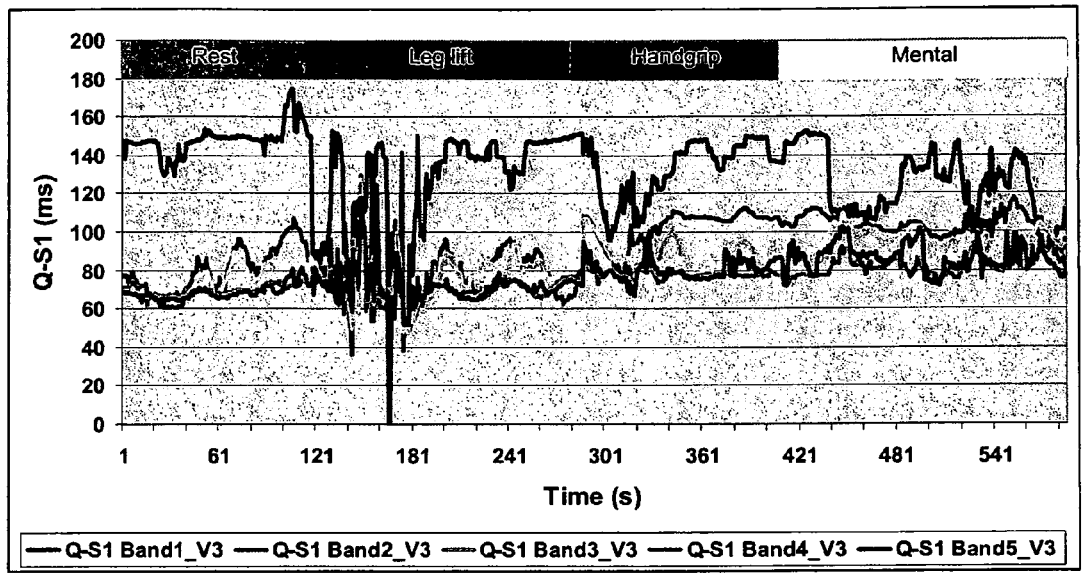
Figure 52:
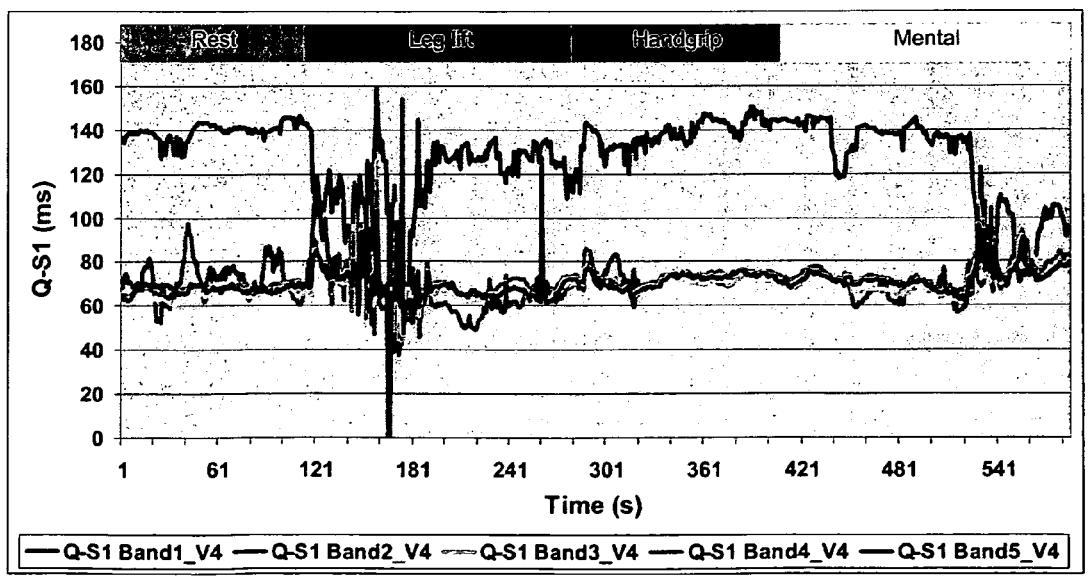
Figure 53:
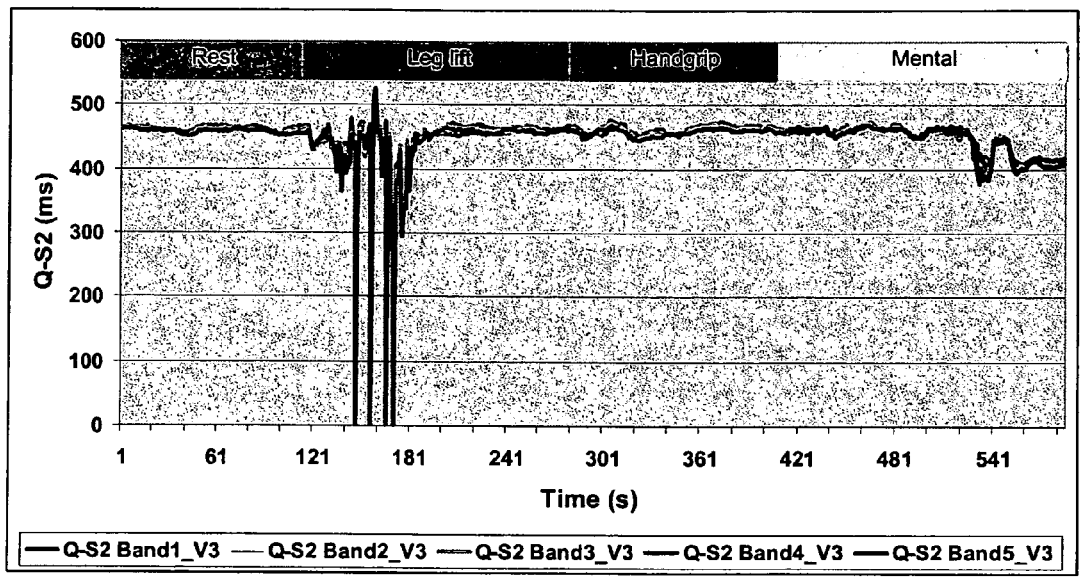
Figure 54:
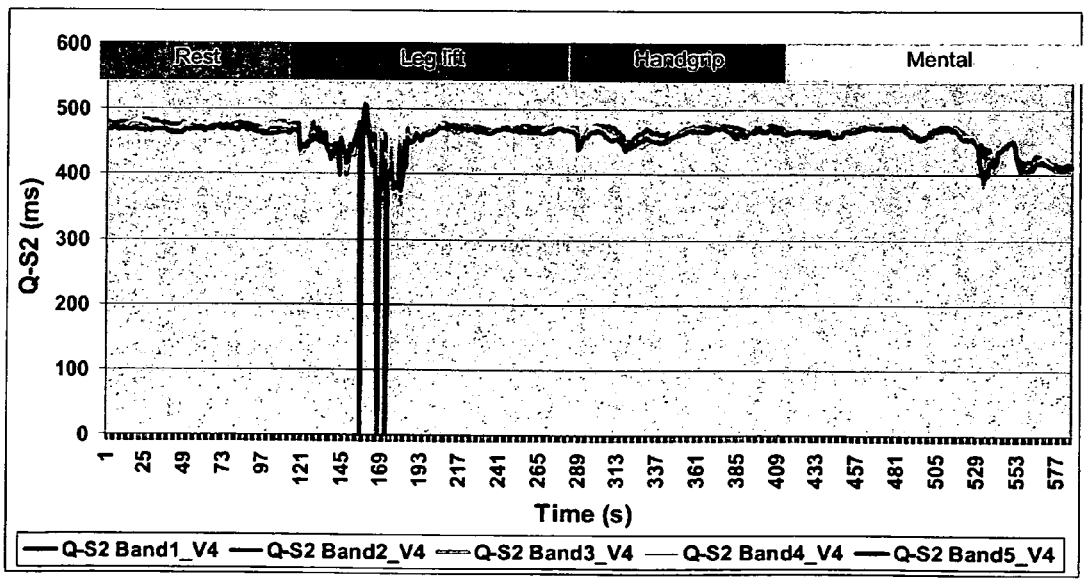
Figure 55:
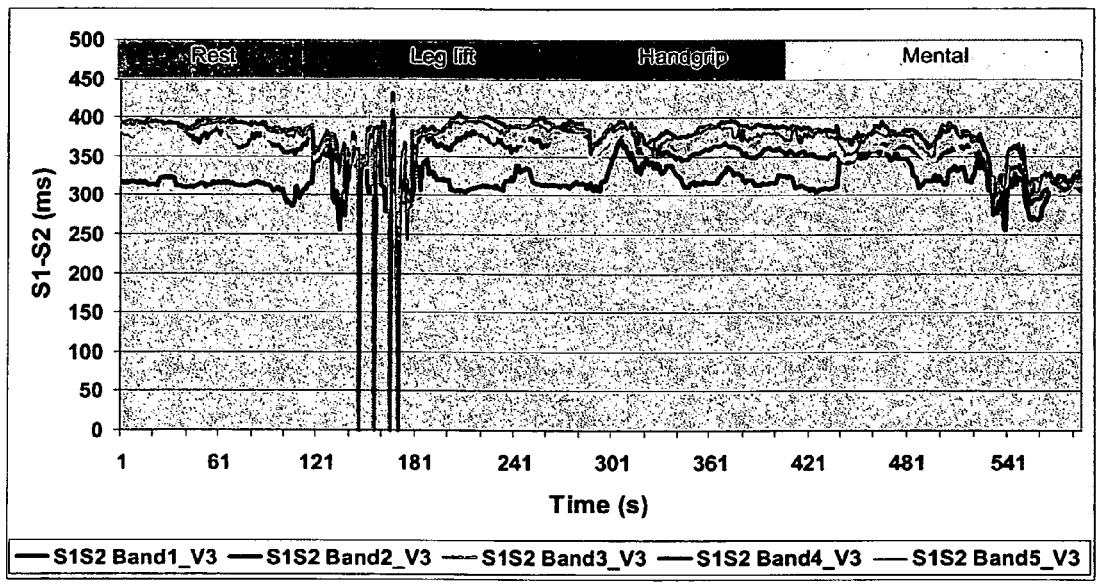
Figure 56:
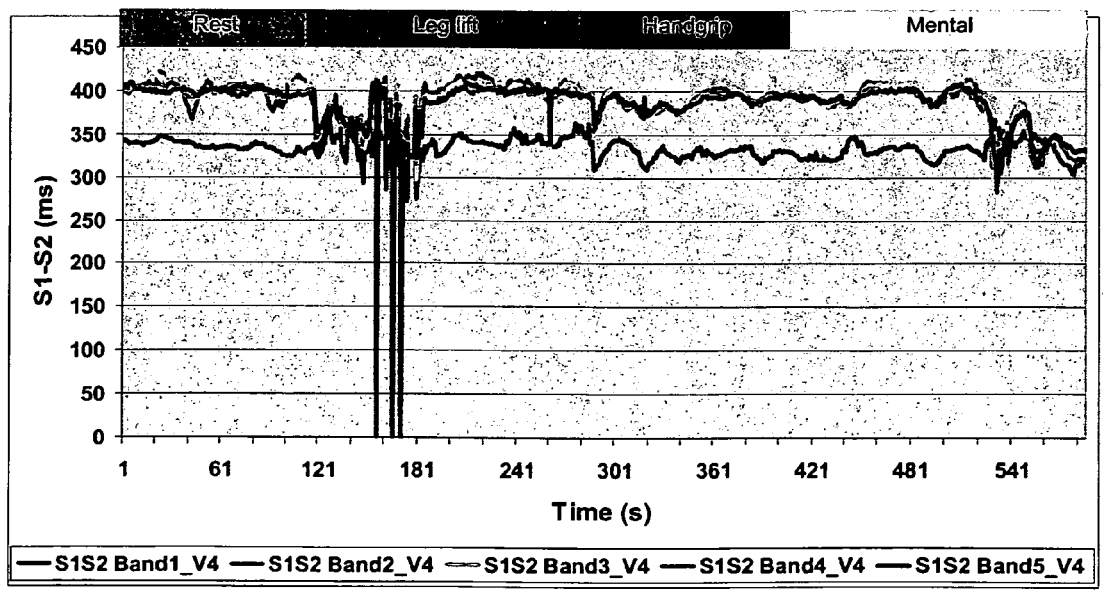

More recently, Tei (Tei C, New non-invasive index for combined systolic and diastolic ventricular function, 1995, J Cardiol, 26:396–404) and others have been evaluating another method to assess left ventricular function using echo parameters as shown in FIG. 6 herein. From Koyama et al, Circulation 2002.

Regarding FIG. 6, this shows measurements of Doppler time intervals, Doppler-derived index of combined systolic and diastolic myocardial performance (Tei Index), and indexes of pulmonary venous flow. Tei Index, as set forth immediately below, was calculated as sum of isovolumic contraction time and isovolumic relaxation time divided by ejection time. PCG indicates phonocardiogram; ICT, isovolumic contraction time; IRT, isovolumic relaxation time; ET, ejection time; PVF, pulmonary venous flow; S, systolic wave; D, diastolic wave; and A, atrial wave:

$$\text{Tei Index} = (ICT + IRT)/ET$$

The Tei Index, the establishment of which is relatively time-consuming and expensive, uses a combination of systolic and diastolic time intervals to create a ratio that has been used to diagnose left ventricular dysfunction, or as a non-invasive means for evaluation of ejection fraction. (Lax et al, Estimation of ejection fraction in patients with myocardial infarction obtained from a combined index of systolic and diastolic left ventricular function, 2000, J Am Soc Echocardiogr, 13(2): 116–123). The Tei Index is simply the sum of isovolumic contraction time (time from start of electrical systole to time of start of ejection) and isovolumic relaxation time (time of end of ejection to start of filling in diastole) divided by ejection time during systole. The literature has used thresholds near 0.5 to define normal from abnormal LV function.

The method proposed and implemented by practice of the present invention involves using a combination of ECG and heart sounds in a manner which is somewhat mathematically similar to the Tei Index to assess LV function. We refer to this as the LVF Index, and it is defined as:

LVF Index=$(QS1+S2S3)/(QS2-QS1)$

QS1 is the time from Q onset on the ECG (the onset of electrical contraction in systole) to the first heart sound (S1). This time interval plus a small delta (delta-1) is equal to isovolumic contraction time. S2S3 is the time interval from the second heart sound, S2, to the third heart sound, S3. This time interval is equal to isovolumic relaxation time plus a small delta, delta-2. QS2 is the time from Q onset on the ECG to the second heart sound, S2, that is a marker of the end of ejection time. The time QS2 minus QS1 is then similar to ejection time plus the same small difference, delta-1.

It would be expected that the small delta-2 difference between S2S3 would not be significant in the overall calculation—and the small delta-1 is present in both the numerator and denominator, and therefore, its impact even more minimized.

Calculation of our LVF Index is quick and inexpensive. This LVF Index, we believe, can be used non-invasively as a means to evaluate a person's improvement with medications for heart failure, for example, or to track that person's development of a worsening LV function. It can also be used to develop a diagnostic metric for detection of LV dysfunction or heart failure in combination with other sound and ECG parameters.

Thus, one can readily see that by capturing, correlating, and otherwise examining and processing selected aspects and elements from a person's electrical and acoustical heart signatures, it is possible to monitor and characterize, in great depth, much about the condition of that person's heart. Even though there is certainly much to learn about the significances of various elements which can be drawn from such signatures, and which can be interrelated cooperatively, it should be clear that the present invention opens a new and powerful door for heart-condition examination.

LITERATURE REFERENCES

In much of the text above, various references are made to relevant literature which publishes the research of a number of people. Set forth immediately below are detailed identifications of these and other useful publications:

Bennett E D, Smithen C R, Sowton E. Significance of Atrial Sound in Acute Myocardial Infarction. Proceedings of the British Cardiac Society, 34(2): 202, 1972.

Schapira J N, Fowles R E, Bowden R E, Alderman E L, Popp R L. Relation of P-S4 Interval to Left Ventricular End-Diastolic Pressure. British Heart Journal 47:270–276, 1982.

Toutouzas P, Gupta D, Samson R, Shillingford J. Q-second sound interval in acute myocardial infarction. British Heart Journal, 31:4, 1969, 462–467.

Hamosh P, Cohn J N, Engelman K, Broder M I. Systolic Time Intervals and Left Ventricular Function in Acute Myocardial Infarction. Circulation, 1972, 45(2): 375–381.

Bennett E D, Smithen C R, Sowton E. The Use of Systolic Time Intervals as an Assessment of Left Ventricular Function in Acute Myocardial Infarction. Medical Research Society (Clinical Science) 40(6): 24–25, 1971.

Samson R. Changes in Systolic Time Intervals in Acute Myocardial Infarction. British Heart Journal 32:839, 1970.

Wertheimer L. Non-invasive Techniques in the Diagnosis and Management of Acute Cardiac Problems. Medical Clinics of North America, 57(6): 1491–1501, 1973.

Weissler A M, Harris W S, Schoenfield C D. Systolic Time Intervals in Heart Failure in Man. Circulation 37: 149, 1968.

Hodges M, Halpern B L, Friesinger G C et al. Left ventricular Pre-Ejection Period and Ejection Time in Patients with Acute Myocardial Infarction. Circulation 45:929, 1972.

Heikkila J, Luomanmaki K, Pyorala K. Serial Observations on Left Ventricular Dysfunction in Acute Myocardial Infarction II. Systolic Time Intervals in Power Failure. Circulation 44(3): 343–354, 1971.

Stein P D, Sabbah H N, Barr I. Intensity of Heart Sounds in the Evaluation of Patients Following Myocardial Infarction. Chest 75(6): 679–684, 1979

Price W H, Brown A E. Alterations in Intensity of Heart Sounds After Myocardial Infarction. British Heart Journal 30:835–9, 1968.

Kusukawa R, Bruce D W, Sakamoto T, MacCanon D M, Luisada A A. Hemodynamic Determinants of the Amplitude of the Second Heart Sound. J of Applied Physiology 21:938–946 1965.

Perloff J K, Reichek N, Value and limitations of systolic time intervals (pre-ejection period and ejection time) in patients with acute myocardial infarction. Editorial. Circulation, 1972, 45: 929.

Luisada A A: The second heart sound in normal and abnormal conditions. American Journal of Cardiology. 1971, 28: 150–161.

Lewis R P, Rittgers S E, Forester W F, et al: A critical review of the systolic time intervals. Circulation 56: 146–158, 1977.

Sakamoto T, Kusukawa R, MacCanon D M et al: Hemodynamic determinants of the amplitude of the first heart sound. Circulation Research, 1965, 16: 45–57.

Luomanmaki K, Heikkila J: Duration of the phases of left ventricular mechanical systole in healthy men aged 45 to 64 years. Annals of Clinical Research 1: 156, 1969.

Friedman S A, Davison E T: The phonocardiographic assessment of myocardial function in the aged. American Heart Journal, 1969, 78:752.

Parmley W W, Diamond G, Tomoda H, Forrester J S, Swan H J C: Clinical evaluation of left ventricular pressures in myocardial infarction. Circulation. 1972, 45: 358.

Bonner A J, Sacks H N, Tavel M E: Assessing the severity of aortic stenosis by phonocardiography and external carotid pulse recording. Circulation, 1973, 48: 247.

Goldblatt A, Aygen M M, Braunwald E: Hemodynamic-phonocardiographic correlations of the fourth heart sound in aortic stenosis. Circulation 26: 91, 1962.

Perez G L, Luisada A A. When Does a Fourth Sound Become an Atrial Gallop? Angiology, 27(5): 300–310, 1976.

Goldman and Braunwald, Primary Cardiology. W.B. Saunders Company, 1998.

Stein P D, Sabbah H N, Barr I. Intensity of Heart Sounds in the Evaluation of Patients Following Myocardial Infarction. Chest 75(6): 679–684, 1979.

Sigwart U, Grbic M, Payot M, Goy J, Essinger A, Fischer A. Ischemic Events During Coronary Artery Balloon Obstruction.

Hauser A M, Gangadharan V, Ramos R, Gordon S, Timmis G. Sequence of Mechanical, Electrocardiographic and Clinical Effects of Repeated Coronary Artery Occlusion in Human Beings. JACC, 5 (2): 193–197, 1985.

Barry W H, Brooker J Z, Alderman E L, Harrison D C. Changes in Diastolic Stiffness and Tone of the Left Ventricle During Angina Pectoris. Circulation 55:761–6, 1974.

Perloff J K, Talano J V, Ronan J A. Noninvasive Techniques in Acute Myocardial Infarction. Progress in Cardiovascular Disease 13(5): 437–464, 1971.

Maisel A S, Gilpin E A, Klein L, Le Winter M, Henning H, Collins D. The murmur of papillary muscle dysfunction in acute myocardial infarction: Clinical features and prognostic implications. American Heart Journal 1986, 112: 705–711.

Julian, D. G., J. C. Cowan, et al. (1998). Cardiology. Edinburgh; New York, W.B. Saunders Co.

Craige E. The Fourth Heart Sound in Lean DF, Shaver J A (eds): American Heart Association Monograph No. 46. New York, American Heart Association, 1975, P. 74–78.

CONTINUED DESCRIPTION OF THE INVENTION

FIG. 8 in the drawings illustrates a printed, strip-chart-like output report—a report providing, in addition to various otherwise known graphical and pictorial pieces of information, specific additional isolated and focused report information including graphical elements 202, and text components 204, based upon the acoustical and electrical signature and fingerprinting practice offered and implemented by practice of the present invention.

Various other kinds of outputs, report, etc. can be constructed as well, such as electronic files for archival purposes relating to a particular subject. For example, in recalling that one of the practices proposed by the present invention involves comparing current signature fingerprint information of a particular person with previously acquired similar fingerprints, one can appreciate the added value which the present invention offers to medical practitioners, with respect to serial tracking of a person's heart condition.

FIGS. 9–32, inclusive, provide a plurality of time-based, different specific fingerprints drawn from the acoustical and electrical signatures of a person represented herein as Subject A. The pre-known characteristics of Subject A were: (a) male, 36-years old; (b) presenting symptoms—chest pain and dyspnea II; (c) echo findings—normal heart anatomy with good systolic and diastolic, EF:56; (d) BNP:12.

Each fingerprint presentation in this collection of drawing figures illustrates how fingerprint character changes under different Subject "conditions" including (a) an at-rest condition, and additionally, three different stress conditions created by (b) a leg lift, (c) an isometric hand grip, and (d) a conventional mental stress condition, such as one resulting from a request that a certain string of numbers be repeated in reverse.

By way of contrast and comparison, FIGS. 33–56, inclusive, illustrate the same several categories of plural, time-based fingerprints, but here drawn from the acoustical and electrical signatures and fingerprints derived from another person represented herein as Subject B. The pre-known characterizations of Subject B were: (a) female, 79-years old; (b) presenting symptoms—angina pectoris II, palpitations, pre-surgery evaluation; (c) echo findings—mild aortic insufficiency with aortic sclerosis and borderline sinus ectasia; (d) good systolic function, impaired diastolic relaxation with normal LVEDP, no LV, EF:60, (e) BNP: 110.

Accordingly, it should be apparent that the present invention, in respect both of its structure and its methodology, provides a deep and robust tool for monitoring, characterizing, and aiding in understanding, a subject's heart condition. Among other important contributions to the art, the present invention significantly addresses the issue of performing ECG and heart-acoustic parameter measurements under precise computer and software control, rather than by imprecise, individual hand measurements conducted on and with respect to printed paper representations of ECG and acoustic data.

From the above description of the invention, and from a review of the associated drawings herein, the structural aspects of the invention can be expressed as a system including acoustic and electrical data-gathering devices employable to collect acoustic and electrical data from a person, and processing structure operatively connected to these devices, and operable to process and correlate data gathered by these devices for the purpose of generating a reportable heart-condition fingerprint of a person from whom such data has been collected. These data-gathering devices each includes an appropriate data-gathering structure, and the respective, associated data-gathering structures are, selectively, one of (a) noninvasive and (b) invasive.

From a methodologic point of view, the invention can be expressed as a method for monitoring and characterizing a person's heart condition for various medically related purposes, including the steps of (a) acquiring a selected person's acoustic heart signature, (b) acquiring, substantially simultaneously, that same person's electrical heart signature, (c) choosing elements of determined interest from these two acquired signatures and selectively processing and/or correlating such elements, and (d) employing the results of the processing and correlating activity to create a heart-condition fingerprint (at least one) which is useful in the characterization of that person's heart condition. Preferably, and wherever appropriate, computer structure and activity is employed in the implementing of the practice of the invention.

Included non-exhaustively among the mentioned elements of determined interest, and associated processing and correlation results, are (a) heart sounds S1, S2, S3 and S4, (b) heart-sound (1) durations, (2) energy contents, (3) relative amplitudes, (4) frequency content, (5) relative frequency content, and (c) sound/sound, ECG/EGC, sound/ECG, and ECG/sound time intervals and relative ratios.

Still another way of expressing the methodology of the invention is to describe it as offering a method for aiding in monitoring and characterizing a person's heart condition, including the steps of (a) furnishing noninvasive data-gathering access to a selected person's heart, and (b) following that furnishing activity, and utilizing the furnished access, gathering, processing and correlating selected portions of data reflecting that person's heart-generated mechanical and electrical behaviors.

Yet another way of expressing the methodology of the invention is to describe it as a method for aiding in monitoring and characterizing a person's heart condition, including the steps of (a) furnishing invasive data-gathering access to a selected person's heart, and (b) thereafter, and utilizing such furnished access, gathering, processing and correlating selected portions of that data reflecting the associated person's heart-generated mechanical and electrical behaviors.

Still a further way of viewing the methodology of the present invention is to see it as a method employing the combined monitoring and characterizing advantages which are derived from processing of electrical and mechanical heart-activity data for promoting the monitoring and characterizing of a person's heart condition in relation to a population of known, different heart afflictions, with this method including the steps of (a) collecting a body of heart-activity-related electrical data which is associated with a selected person's heart, and recognizing that such electrical data possesses both monitoring and characterizing strengths and weaknesses with regard to a first category of certain ones of such heart afflictions, (b) collecting, substantially simultaneously, a body of heart-activity-related mechanical data associated with that same person's heart, and time-related with respect to such collected electrical data, and recognizing that such mechanical data also possesses both monitoring and characterizing strengths and weaknesses with regard to a different, second category of certain ones of such heart afflictions, and (c) correlating, for monitoring and characterizing purposes, such collected electrical and mechanical data bodies in a manner whereby, collectively, the strengths of each data body tend to compensate for the weaknesses of the other data body.

Accordingly, a preferred and best mode embodiment and manner of practicing the present invention have been fully described and illustrated herein. And, while this is the case, we fully recognize that those generally skilled in this art may well think about and choose to implement many variations and modifications of the system, all of which will come within the scope of the invention.

We claim:

1. A method for monitoring and characterizing a person's heart condition for various medically related purposes comprising acquiring a selected person's acoustic heart signature, acquiring, substantially simultaneously, that same person's electrical heart signature, choosing elements of determined interest from these two acquired signatures and selectively processing and relating such elements, and employing the results of said relating step to create a heart-condition fingerprint useful in the characterization of that person's heart condition, the above-mentioned steps being performed in such a manner whereby (a) said two acquiring steps are performed in continuity over a predetermined time interval, (b) said choosing, processing and relating steps are performed in a manner designed to create time-dependent relationship results, and (c) said employing step is performed in a manner designed to generate a time-dependent, heart-condition fingerprint.

2. The method of claim 1 which further comprises utilizing the created fingerprint to effect control over a selectable medically-related interaction with the person.

3. The method of claim 1, wherein said two acquiring steps are performed under circumstances with the person placed in a selected stress condition.

4. The method of claim 1, wherein such elements of determined interest and such processing and relating results include information drawn from the group including (a) heart sounds S1, S2, S3, S4, (b) heart-sound (1) durations, (2) energy content, (3) relative amplitudes, (4) frequency content, (5) relative frequency content, and (c) sound/sound, sound/ECG, ECG/sound and ECG/ECG time intervals and relative ratios.

5. A method for monitoring and characterizing a person's heart condition for various medically related purposes comprising acquiring a selected person's acoustic heart signature, acquiring, substantially simultaneously, that same person's electrical heart signature, choosing elements of determined interest from these two acquired signatures and selectively computer-processing and computer-relating such elements, and employing the results of said relating step to create a heart-condition fingerprint useful in the characterization of that person's heart condition, the above-mentioned steps being performed in such a manner whereby (a) said two acquiring steps are performed in continuity over a predetermined time interval, (b) said choosing, processing and relating steps are performed in a manner designed to create time-dependent relationship results, and (c) said employing step is performed in a manner designed to generate a time-dependent, heart-condition fingerprint.

6. The method of claim 5, wherein said two acquiring steps are performed under circumstances with the person placed in a selected stress condition.

7. The method of claim 5, wherein such elements of determined interest and such processing and relating results include information drawn from the group including (a) heart sounds S1, S2, S3, S4, (b) heart-sound (1) durations, (2) energy content, (3) relative amplitudes, (4) frequency content, (5) relative frequency content, and (c) sound/sound, sound/ECG, ECG/sound and ECG/ECG time intervals and relative ratios.

8. A method for aiding in monitoring and characterizing a person's heart condition comprising furnishing invasive data-gathering access to a selected person's heart, and following said furnishing, and utilizing such access, gathering, processing and relating selected portions of, data reflecting that person's heart-generated mechanical and electrical behaviors.

9. The method of claim 8, wherein at least said relating step involves utilizing computer processing.

10. A method employing the combined monitoring and characterizing advantages derived from possession of electrical and mechanical heart-activity data for promoting the monitoring and characterizing of a person's heart condition in relation to a population of known, different heart afflictions, said method comprising collecting a body of heart-activity-related electrical data associated with a selected person's heart, and recognizing that such electrical data possesses both monitoring and characterizing strengths and weaknesses with regard to a first category of certain ones of such heart afflictions, collecting, substantially simultaneously, a body of heart-activity-related mechanical data associated with that same person's heart, and time-related with respect to such collected electrical data, and recognizing that such mechanical data possesses both monitoring and characterizing strengths and weaknesses with regard to a different, second category of certain ones of such heart afflictions, and processing and relating, for monitoring and characterizing purposes, such collected electrical and mechanical data bodies in a manner whereby, collectively, the strengths of each data body tend to compensate for the weaknesses of the other data body.

11. The method of claim 10, wherein at least said relating step involves utilizing computer processing.

12. A heart-condition monitoring and characterizing method associated generally with an acute coronary syndrome condition, said method comprising during a common time frame, collecting (a) a person's heart-activity-generated, electrical-functionality signature, and (b) that same person's heart-activity-generated, mechanical-functionality signature, processing such signatures in a manner which includes inter- and/or cross-relating selected components of the two signatures, and from said processing, generating a binary output which indicates definitively the presence or absence of acute coronary syndrome respecting the person's heart.

13. A computer-based heart-condition monitoring and characterizing method comprising during a common time frame, collecting (a) a person's heart-activity-generated, electrical-functionality signature data, and (b), that same person's heart-activity-generated, mechanical-functionality signature data, supplying that collected signature data to a computer, and using that computer, processing the supplied signature data in a manner which includes at least one of (a) computer-measuring, (b) computer-evaluating, and (c) computer-inter-relating and/or computer-cross-relating, selected components of the two categories of signature data for the purpose of generating a reportable heart-condition fingerprint of a person from whom such signature data has been collected.

14. A method for monitoring and characterizing a person's heart condition for various medically related purposes comprising acquiring a selected person's acoustic heart signature, acquiring, substantially simultaneously, that same person's electrical heart signature, choosing elements of determined interest from these two acquired signatures and selectively processing and relating such elements, employing the results of said relating step to create a heart-condition fingerprint useful in the characterization of that person's heart condition, and performing time-spaced, serial comparisons between a person's heart-condition fingerprints which have been created at different points in time.

15. A method for monitoring and characterizing a person's heart condition for various medically related purposes comprising acquiring a selected person's acoustic heart signature, acquiring, substantially simultaneously, that same person's electrical heart signature, choosing elements of determined interest from these two acquired signatures and selectively processing and relating such elements, employing the results of said relating step to create a heart-condition fingerprint useful in the characterization of that person's heart condition, and comparing a person's created heart-condition fingerprint with a like fingerprint contained in a database derived previously from practice of the method with a defined population of individuals.

* * * * *